(12) United States Patent
Littleton et al.

(10) Patent No.: US 9,758,788 B2
(45) Date of Patent: Sep. 12, 2017

(54) MUTAGENESIS OF PLANTS FOR OVERPRODUCTION OF SELECTIVE ESTROGEN RECEPTOR MODULATORS

(71) Applicant: Naprogenix, Inc., Lexington, KY (US)

(72) Inventors: John M. Littleton, Lexington, KY (US); Deane Falcone, Lexington, KY (US); Dustin Brown, Lexington, KY (US); Samir Gunjan, Lexington, KY (US); Trent Rogers, Lexington, KY (US)

(73) Assignee: Naprogenix, Inc., Lexington, KY (US)

( * ) Notice: Subject to any disclaimer, the term of this patent is extended or adjusted under 35 U.S.C. 154(b) by 0 days.

(21) Appl. No.: 14/821,461

(22) Filed: Aug. 7, 2015

(65) Prior Publication Data
US 2016/0040176 A1    Feb. 11, 2016

Related U.S. Application Data

(60) Provisional application No. 62/035,207, filed on Aug. 8, 2014.

(51) Int. Cl.
*C12N 15/82* (2006.01)
*C12N 15/01* (2006.01)
*C12N 5/04* (2006.01)

(52) U.S. Cl.
CPC ......... *C12N 15/8209* (2013.01); *C12N 15/01* (2013.01); *C12N 15/821* (2013.01); *C12N 15/8243* (2013.01); *C12N 5/04* (2013.01); *C12N 15/8205* (2013.01)

(58) Field of Classification Search
None
See application file for complete search history.

(56) References Cited

U.S. PATENT DOCUMENTS

| | | | |
|---|---|---|---|
| 6,989,236 B1 | 1/2006 | Falcone et al. | |
| 7,547,520 B2 | 6/2009 | Falcone et al. | |
| 7,737,327 B2 * | 6/2010 | Falcone | C12N 15/8209 435/421 |
| 2011/0152226 A1 * | 6/2011 | Scanlan | C07C 57/42 514/171 |

* cited by examiner

*Primary Examiner* — Cathy Kingdon Worley
(74) *Attorney, Agent, or Firm* — Viksnins Harris Padys Malen LLP

(57) ABSTRACT

Certain embodiments of the invention provide methods of selecting a mutant plant cell that overproduces a compound that activates an estrogen receptor (ER) beta but does not activate an ER alpha.

6 Claims, 2 Drawing Sheets

MUTAGENESIS OF PLANTS FOR OVERPRODUCTION OF SELECTIVE ESTROGEN RECEPTOR MODULATORS

CROSS-REFERENCE TO RELATED APPLICATION

This application claims priority from U.S. Provisional Application No. 62/035,207, filed Aug. 8, 2014, which application is herein incorporated by reference.

GOVERNMENT FUNDING

This invention was made with government support under R41AA014555, R41AA014554, R42AA016739, R41AA015475, R41CA115093, R42AT006639 and R43AA018226 awarded by the National Institutes of Health. The government has certain rights in the invention.

BACKGROUND OF THE INVENTION

Plants produce many small molecules, such as metabolites, with specific and potent biological activity. These molecules are commonly economically important, either because they are valuable commercial products or because they have regulatory functions as plant hormones or intracellular messengers. Therefore, methods have been developed to identify plant metabolites of interest, as well as the genes associated with their production, which combine activation tagging mutagenesis (ATM) and high throughput screening (HTS) (see, e.g., U.S. Pat. Nos. 7,547,520 and 6,989,236). Other methods have been developed to generate and screen plant cell mutants that produce metabolites of interest using a visible marker protein (see, e.g., U.S. Pat. No. 7,737,327). However, these methods require screening large numbers of mutants and/or rely on the subjective nature of visual screening. Accordingly, there is a need for new methods for the discovery and/or production of compounds, such as plant metabolites that may be used as pharmaceuticals, agrochemicals, herbicides and/or nutraceuticals.

SUMMARY OF THE INVENTION

Accordingly certain embodiments of the invention provide a method comprising:

a) transforming cells from a selected plant with a vector comprising a gene encoding a heterologous target protein, to obtain transgenic primary plant cells, wherein the selected plant is from a species that produces activators or inhibitors of the heterologous target protein;

b) mutagenizing an explant obtained from the transgenic primary plant cells to form mutagenized transgenic cells; and c) exposing the mutagenized transgenic cells to a compound, wherein mutagenized transgenic cells that overproduce one or more activators or inhibitors of the heterologous target protein, as compared to a non-mutant transgenic plant cell from the same species, survive; and wherein mutagenized transgenic cells that do not overproduce one or more activators or inhibitors of the heterologous target protein, as compared to a non-mutant transgenic plant cell from the same species, die.

Certain embodiments of the invention provide a method comprising:

a) selecting a species of plant that produces activators or inhibitors of a heterologous target protein;

b) infecting cells (e.g., a seedling) from the selected plant species with *Agrobacterium rhizogenes* comprising a vector comprising a gene encoding the heterologous target protein, to obtain a transgenic primary hairy root;

c) obtaining an explant from the transgenic primary hairy root;

d) infecting the cells from the explant with *Agrobacterium rhizogenes* comprising an activation tagging mutagenesis (ATM) vector, to obtain a transgenic secondary hairy root; and e) exposing the transgenic secondary hairy root to a compound, wherein mutagenized transgenic secondary hairy roots that overproduce an activator or inhibitor of the heterologous target protein, as compared to a non-mutant transgenic hairy root, survive; and wherein mutagenized transgenic secondary hairy roots that do not overproduce an activator or inhibitor of the heterologous target protein, as compared to a non-mutant transgenic hairy root, die.

Certain embodiments provide a method comprising:

a) selecting a species of plant that produces activators of a first heterologous target protein and a second heterologous target protein;

b) transforming cells from the selected plant with a first vector comprising a gene encoding the first heterologous target protein and a gene encoding a selection marker, wherein the activation of the first heterologous target protein is operably linked to the expression of the selection marker, to obtain transgenic primary plant cells;

c) transforming cells from an explant obtained from the transgenic primary plant cells with a second vector comprising a gene encoding the second heterologous target protein and a cell death gene, wherein activation of the second heterologous target protein is operably linked to the expression of the cell death gene, to obtain transgenic secondary plant cells;

d) mutagenizing cells from an explant obtained from the transgenic secondary plant cells to form mutagenized transgenic cells; and e) exposing the mutagenized transgenic cells to a first compound and a second compound, wherein the first compound causes cell death in the absence of the selection marker expression, wherein the second compound causes cell death when the cell death gene is expressed, wherein the mutagenized transgenic cells that overproduce one or more activators of the first heterologous target protein, which are not activators of the second heterologous target protein, survive; wherein overproduction is compared to a non-mutant transgenic plant cell from the same species; and wherein all other cells die.

Certain embodiments of the invention provide a transgenic plant cell, cell line or plant prepared by the method described herein.

Certain embodiments of the invention provide an extract prepared from a plant cell, cell line or plant described herein.

Certain embodiments of the invention provide a method for inhibiting a dopamine transporter, comprising contacting a cell (e.g., a mammalian cell, e.g., a human cell) in vivo or in vitro with lobinaline.

Certain embodiments of the invention provide a method of modulating the activity of a nicotinic receptor for acetylcholine, comprising contacting a cell (e.g., a mammalian cell, e.g., a human cell) in vivo or in vitro with lobinaline.

Certain embodiments of the invention provide a method for treating or preventing a disease or disorder in an animal (e.g., a mammal such as a human) comprising administering an extract comprising lobinaline to the animal.

Certain embodiments of the invention provide a method for treating or preventing a disease or disorder in an animal (e.g., a mammal such as a human) comprising administering lobinaline or a pharmaceutically acceptable salt thereof to the animal.

Certain embodiments of the invention provide a method comprising:

a) transforming plant cells comprising infecting the cells with *Agrobacterium rhizogenes* comprising a first vector comprising a first gene, to obtain a transgenic primary hairy root;

b) obtaining an explant from the transgenic primary hairy root; and c) transforming the explant cells comprising infecting the cells with *Agrobacterium rhizogenes* comprising a second vector comprising a second gene, to obtain a transgenic secondary hairy root.

Certain embodiments of the invention provide a method for the detection of a transgenic protein comprising contacting a transgenic plant cell with a radio-labeled ligand, wherein the ligand is a selective ligand for the transgenic protein.

Certain embodiments of the invention provide a method quantifying of a transgenic protein comprising contacting a transgenic plant cell with a radio-labeled ligand, wherein the ligand is a selective ligand for the transgenic protein.

DETAILED DESCRIPTION

Target-Directed Biosynthesis of Plant Metabolites

Figure 1:
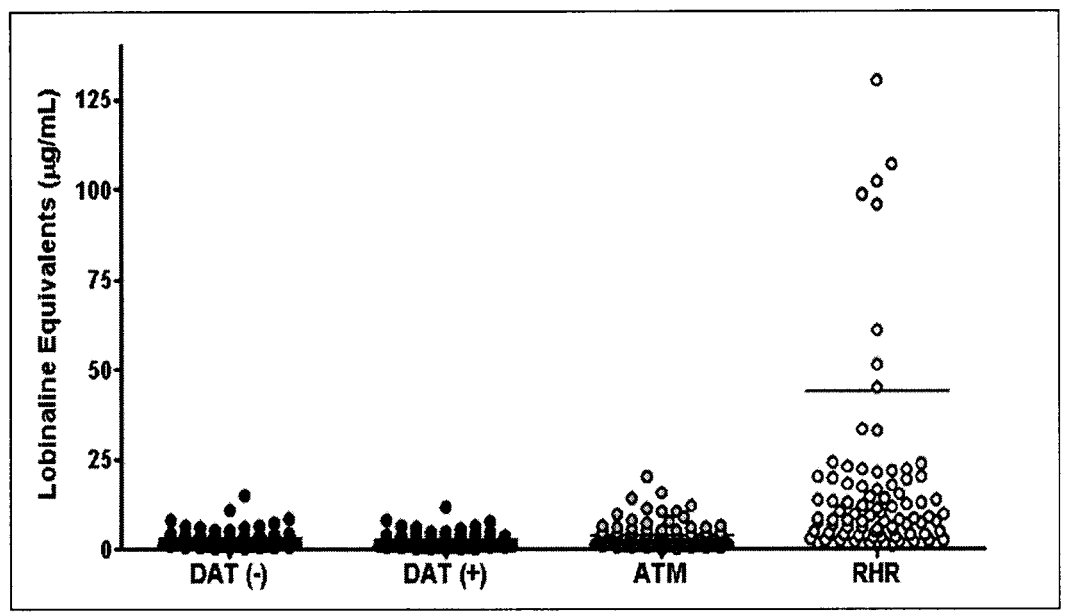
FIG. 1. Scattergram of data obtained for inhibition of [3H]dopamine uptake into rat brain synaptosomes by extracts from individual *Lobelia cardinalis* hairy root cultures from each population. The activity has been expressed as "lobinaline equivalents" based on the activity of 95% pure lobinaline separated from wild-type *L. cardinalis* plants. The populations are: DAT(−) hairy roots generated without the human (h)DAT construct, DAT (+) transgenic hairy roots expressing the human DAT, ATM are transgenic hDAT hairy roots which have been mutated but not selected and RHR ("resistant hairy roots") which are transgenic hDAT hairy roots which have been mutated and generated under selection in 100 uM MPP+. The latter group contains 11 mutants which have such high levels of metabolites which inhibit [3H]dopamine uptake that they cannot be shown on the same scale as the other populations. This contributes to the high mean of the RHR group which is significantly greater than that of any of the other groups.

Described herein are methods relating to the target-directed biosynthesis of plant metabolites. These methods link the interaction of metabolites with a target of interest to a mechanism of plant survival, which enables the selection of mutants that produce metabolites with the required bioactivity. Specifically, a heterologous target is expressed in a mutant plant cell in such a way that activation or inhibition of the target by endogenous metabolites results in survival or death of the plant cell. The aim is to direct the biosynthesis of plant metabolites toward compounds which interact with the heterologous target in a way which has value for human use as, e.g., pharmaceuticals, agrochemicals, herbicides and nutraceuticals. For example, this technology may be used either for compound discovery or for the production of known or novel active metabolites.

Accordingly, certain embodiments of the invention provide a method comprising:

a) transforming cells from a selected plant with a vector comprising a gene encoding a heterologous target, to obtain transgenic primary plant cells, wherein the selected plant is from a species that produces activators or inhibitors of the heterologous target;

b) mutagenizing an explant obtained from the transgenic primary plant cells to form mutagenized transgenic cells; and c) exposing the mutagenized transgenic cells to a compound, wherein mutagenized transgenic cells that overproduce one or more activators or inhibitors of the heterologous target, as compared to a non-mutant transgenic plant cell from the same species, survive; and wherein mutagenized transgenic cells that do not overproduce one or more activators or inhibitors of the heterologous target, as compared to a non-mutant transgenic plant cell from the same species, die.

In certain embodiments, the heterologous target is a protein or nucleic acid. In certain embodiments, the heterologous target is a protein.

Accordingly, certain embodiments of the invention provide a method comprising:

a) transforming cells from a selected plant with a vector comprising a gene encoding a heterologous target protein, to obtain transgenic primary plant cells, wherein the selected plant is from a species that produces activators or inhibitors of the heterologous target protein;

b) mutagenizing an explant obtained from the transgenic primary plant cells to form mutagenized transgenic cells; and c) exposing the mutagenized transgenic cells to a compound, wherein mutagenized transgenic cells that overproduce one or more activators or inhibitors of the heterologous target protein, as compared to a non-mutant transgenic plant cell from the same species, survive; and wherein mutagenized transgenic cells that do not overproduce one or more activators or inhibitors of the heterologous target protein, as compared to a non-mutant transgenic plant cell from the same species, die.

In certain embodiments of the invention, the mutagenized transgenic cells overproduce one or more activators of the heterologous target protein. As used herein, the term "activator" refers to a molecule capable of stimulating the function of a heterologous target protein. Activators may interact directly (e.g., by binding) or indirectly with the heterologous target protein and include, for example, agonists, partial agonists or co-factors of the heterologous target protein. As used herein, a partial agonist is a molecule that may activate the heterologous target protein (e.g., by binding to the target protein), but has lower or incomplete efficacy as compared to a full agonist.

In certain embodiments of the invention, the mutagenized transgenic cells overproduce one or more inhibitors of the heterologous target protein. As used herein, the term "inhibitor" refers to a molecule capable of reducing the function of a heterologous target protein. Inhibitors may interact directly (e.g., by binding) or indirectly with the heterologous target protein and include, for example, antagonists or partial antagonists of the heterologous target protein. As used herein, a partial antagonist is a molecule that may reduce the activity of the heterologous target protein (e.g., by binding to the target protein) when this is stimulated by an agonist, but has lower or incomplete efficacy as compared to a full antagonist.

Plant Selection and Transformation

The term "plant" is used to refer to any of the various photosynthetic, eukaryotic, multicellular organisms of the kingdom Plantae. The term may be used to refer to the entire organism or to a portion thereof, such a root or an individual cell.

As described herein the selected plant is from a species that produces activators or inhibitors of the heterologous target protein. Any plant species may be used in the methods described herein if it is capable of producing activators or inhibitors of the heterologous target protein. Thus, the species of plant selected for use in the methods described herein is based on the choice of the heterologous target protein.

Accordingly, in certain embodiments, the methods further comprise selecting a species of plant that produces activators or inhibitors of the heterologous target protein. Experiments and assays for determining whether a species of plant produces activators or inhibitors of a heterologous target protein are known in the art. For example, a radioligand displacement assay (Gattu et al. 1995, J. Neurosci. Meth. 63:121-125) or a functional assay may be used to evaluate a given plant extract in relation to a certain heterologous target protein. Thus, in certain embodiments, the plant species is selected by screening an extract library of plant species for activators or inhibitors of the heterologous target protein (e.g., using a radioligand displacement assay or a functional assay) (see, e.g., Example 1).

In certain embodiments, the selected plant is a *Lobelia cardinalis, Hypericum punctatum, Nicotiana tabacum, Glycine max* or *Glycyrrhiza glabra*.

Cells from a selected plant may be transformed with a vector using techniques and methods known in the art (e.g., by *Agrobacterium*, viral transformation, a gene gun or electroporation). In certain embodiments, transformation may be performed by infecting the plant cells with *Agrobacterium* comprising the vector, to obtain primary transgenic plant cells. In certain embodiments, transformation may be performed by infecting the plant cells with *Agrobacterium rhizogenes* comprising the vector, to obtain primary transgenic hairy roots. For example, in certain embodiments, the plant cells are infected by wounding the plant (e.g., 2, 3, 4 or more times) and soaking it in a solution of *Agrobacterium rhizogenes* comprising the vector (see, e.g., Example 1; Mary C. Christey, Robert H. Braun (2004): Production of Hairy Root Cultures and Transgenic Plants by *Agrobacterium rhizogenes*—Mediated Transformation. Methods in Molecular Biology. Transgenic Plants: Methods and Protocols. Vol. 286. pp 47-60). In certain embodiments, the *A. rhizogenes* strain is R1000, AR1000, A4 or K599. In certain embodiments, the *A. rhizogenes* strain is AR1000, A4 or K599.

In certain embodiments, plant seedlings are used for the transformation (e.g., 4-6 week old seedlings). In certain embodiments, only a portion of the plant is used for the transformation. For example, in certain embodiments, hypocotyl segments from plant seedlings are used for the transformation.

In certain embodiments, the vector comprising the gene encoding the heterologous target protein further comprises a promoter operably linked to the gene (e.g., a promoter that is functional in the selected plant species, e.g., a CaMV 35S promoter.

In certain embodiments, the vector is an *Agrobacterium* binary vector. In certain embodiments, the vector is pCambia 2301, pCambia 2300, pCambia 1300, pKYLX71, pCambia1301-35S or pCambia2301-35S. In certain embodiments, the vector is pCambia1301.

In certain embodiments, the methods further comprise introducing the vector comprising the gene encoding the heterologous target protein into Agrobacteria.

In certain embodiments, the methods further comprise detecting or quantifying the expression of the heterologous target gene and/or protein in the primary transgenic plant cells. In certain embodiments, this characterization is performed prior to mutagenizing an explant obtained from the transgenic primary plant cells. Methods for characterizing the expression of a heterologous target protein/gene are known in the art. For example, expression may be evaluated by preparing a crude extract from the transgenic primary plant cells and evaluating the extract by RT-PCR, Real-Time quantitative RT-PCR or Western blot analysis. Alternatively, as described herein, detection and/or quantification of the expression of the heterologous target protein in the transgenic primary plant cells may be performed using a selective radioligand (see, e.g., Example 1).

In certain embodiments, the methods further comprise examining the functionality of the heterologous target protein expressed in the primary transgenic plant cells (e.g., by examining a crude extract obtained from the cells). As discussed above, functional assays are known in the art and would be tailored to the specific heterologous target protein (e.g., a dopamine transporter would be evaluated to determine whether it possessed the capability to transport dopamine, e.g., radiolabeled dopamine (see, e.g., Example 1)).

In certain embodiments, the methods further comprise obtaining an explant (e.g., 0.5-5 cm explants or 1.5-2 cm explants) from the transgenic primary plant cells. As used herein, the term "explant" refers to any portion of a plant that may be used to initiate a culture (e.g., a portion of a shoot, leaves, roots, or a sample of cells).

In certain embodiments, the explant is obtained from a transgenic primary plant regenerated from the transgenic primary plant cells. In certain embodiments, only partial regeneration is performed prior to obtaining an explant. As described herein, it is possible to generate transgenic primary hairy roots and sequentially transform them to generate transgenic secondary hairy roots, thereby eliminating the need for plant regeneration prior to the secondary transformation. Accordingly, in certain other embodiments, the transgenic primary cells are not regenerated into a transgenic primary plant prior to obtaining an explant (e.g., an explant is obtained directly from a transgenic primary hairy root).

Generation of Mutagenized Transgenic Cells and Exposure to the Compound

The methods described herein comprise the step of mutagenizing an explant obtained from the transgenic primary plant cells (e.g., from a transgenic primary hairy root) to form mutagenized transgenic cells. Methods and techniques for mutagenizing plant cells are known in art (e.g., through the use of chemical mutagens, radiation or by activation tagging mutagenesis (ATM)).

In certain embodiments, the explant is mutagenized by ATM (see, e.g., Example 1). The basic method for activation mutagenesis is known in the art (Fritze and Walden 1995, Meth. Mol. Biol., 44:281-294; Fritze et al. 1995, Plant J., 7:261-271; Walden et al. 1995, Meth. Cell Biol., 49:455-469, each incorporated herein by reference). In this technique, enhancer sequences from the Cauliflower mosaic virus 35S promoter are incorporated (via *Agrobacterium* mediated T-DNA transfer) at random into the plant genome, and produce activation of genes in the immediate vicinity of the incorporated DNA. Because the enhancers cause deregulation of promoters nearby, gene overexpression generally results, usually conferring a dominant, gain-of-function mutation that is immediately scorable, making this mutagenesis technique ideally suited for conducting screens at the callus, root (e.g., hairy root) or individual cell level. Activation of promoters has been found to occur up to 3.6-kb from the T-DNA insert in *Arabidopsis* and the enhancers function independent of orientation, leading to gene overexpression either upstream or downstream from the T-DNA integration site (Weigel et al. 2000). In addition, because the relevant locus is "tagged" with the inserted T-DNA element, a variety of techniques exist to enable the straightforward recovery of the associated genomic DNA, including plasmid rescue or genomic walking.

In certain embodiments, the explant cells are transformed with an ATM vector. ATM vectors, such as PCVICEn4HPT (Hayashi et al. Science, 258(5086): 1350-3 (1992)), are known in the art. Typically, ATM vectors comprise enhancer elements, for example enhancer sequences from the Cauliflower mosaic virus 35S promoter, as well as a selectable marker, such as an antibiotic resistance gene. In certain embodiments, the ATM vector is a binary vector. In certain embodiments, the ATM vector is PCVICEn4HPT, pTP1 or pTPEn4. In certain embodiments, the ATM vector is comprises rol genes, e.g. PCVICEn4HPT comprising rol genes.

In certain embodiments, the methods further comprise introducing the ATM vector into Agrobacteria.

In certain embodiments, transformation is performed by infecting the explant cells with *Agrobacterium* comprising the ATM vector, to form mutagenized transgenic cells. In certain embodiments, transformation is performed by infecting the explant cells with *Agrobacterium rhizogenes* comprising the ATM vector, to form the mutagenized transgenic cells (i.e., transgenic secondary hairy roots (see, e.g., Example 1; explants from transgenic primary hairy roots are wounded multiple times (e.g., 2, 3, 4 or more times) while in a solution of *A. rhizogenes* carrying the ATM vector to generate the transgenic secondary hairy roots)). In certain embodiments, the *A. rhizogenes* strain is R1000, AR1000, A4 or K599. In certain embodiments, the *A. rhizogenes* strain is AR1000, A4 or K599.

In certain embodiments, the methods further comprise culturing the infected explants on a plant growth medium comprising a selection agent, which corresponds to a selection marker in the ATM vector (e.g., an antibiotic, wherein the selection marker is an antibiotic resistance gene). In certain embodiments, the infected explants are maintained on plant growth medium that does not comprise a selection marker for a period of time after infection (e.g., about 6 hrs, 12 hrs, 1 day, 2 days, 3 days, 4 days or more) to allow the transformation event to transpire, and then are transferred to a plant growth medium comprising the selection agent. Typically, small nodules emerge from the transgenic primary hairy roots wound sites within, e.g., about 1 week, 2 weeks, 3 weeks, of the transformation, each representing the initiation of a transgenic secondary hairy root (i.e., expresses the transgenic heterologous target protein and a mutation). Upon the emergence of the nodules, the explants are transferred to a selection medium that comprises both the selection agent (e.g., antibiotic) and the compound, which ensures that only cells with mutations that result in the overproduction of one or more activators or inhibitors of the heterologous target protein survive and develop into a mature transgenic secondary hairy roots.

Thus, as described herein, the method comprises exposing the mutagenized cells to a compound, wherein mutagenized transgenic cells that overproduce one or more activators or inhibitors of the heterologous target protein, as compared to a non-mutant transgenic plant cell from the same species, survive; and wherein mutagenized transgenic cells that do not overproduce one or more activators or inhibitors of the heterologous target protein, as compared to a non-mutant transgenic plant cell from the same species, die. In certain embodiments of the invention the method comprises exposing the mutagenized transgenic cells to both a selection agent (e.g., an antibiotic) and the compound (e.g., growth medium comprising a selection agent and the compound). In certain embodiments, the mutagenized transgenic cells (e.g., the transgenic secondary hairy roots) are exposed to the compound for about 1, 2, 3, 4, 5 or 6 days, or 2, 3, 4, 5, or 6 weeks, or 2, 3, 4, 5, 6, 7 or 8 months or more to ensure the stability of the phenotype of the mutagenized transgenic cells (e.g., are maintained in growth medium comprising the compound).

In certain embodiments, the method further comprises obtaining a crude extract from the mutagenized transgenic cells exposed to the compound. In certain embodiments, the exposed mutagenized transgenic cells are maintained on a growth medium lacking the compound for a period of time prior to obtaining the crude extract (e.g., about 1, 2, 3, 4, 5 or 6 weeks, or 2, 3, 4, 5 or 6 months or more). This ensures that residual amounts of the compound are not present in the crude extracts, which may be analyzed for chemical or pharmacological characteristics.

In certain embodiments, the crude extracts obtained from the mutagenized transgenic cells exposed to the compound, are analyzed for pharmacological and/or chemical characteristics. In certain embodiments, the method further comprises identifying one or more activators or inhibitors that are overproduced in the mutagenized transgenic cells (e.g., by screening HPLC fractions obtained from the crude extracts and/or chemical analysis of the crude extracts by GC/MS). In certain embodiments, the pharmacological properties of the crude extracts are analyzed (e.g., using functional assays tailored to the heterologous target protein (see, e.g., Example 1)).

Additionally, in certain embodiments, the method further comprises identifying the specific mutation (e.g., the mutation that causes the overproduction of the one or more activators or inhibitors of the heterologous target protein) unique to each mutagenized transgenic cell population (e.g., each transgenic secondary hairy root) using techniques known in the art (see, e.g., U.S. Pat. No. 7,737,327, which is incorporated herein by reference). For example, genomic DNA may be isolated from the crude extracts and DNA adjacent to the activation T-DNA tag may be recovered by, e.g., plasmid rescue or genomic walking, and sequenced. Additionally, genomic DNA may be sequenced by high throughput DNA sequencing and compared to genomic DNA obtained from non-transgenic plant cells of the same species, to identify the relevant mutation. For example, mutations may be located in known regulator genes, previously unknown regulator genes or in genes that have only indirect effects on the pathways associated with the heterologous target protein. Characterization of these mutations may be used to help elucidate the relevant metabolic pathways. Additionally, characterization of the T-DNA and flanking sequences will provide new information regarding gene structure and organization.

In certain embodiments, the method further comprises analyzing the expression of a set of genes in the crude extract obtained from the exposed mutagenized transgenic cells with a crude extract obtained from non-transgenic plant cells of the same species (e.g., by using an array).

In certain embodiments, the method further comprises regenerating a plant from the exposed mutagenized transgenic cells (e.g., from the transgenic secondary hairy roots, which survived the compound exposure).

Heterologous Target Proteins and Associated Compounds for Selection

Described herein are methods for the directed biosynthesis of plant metabolites toward activators or inhibitors of a heterologous target protein, which have value for human use as, e.g., pharmaceuticals, agrochemicals, herbicides or nutraceuticals. Accordingly, in certain embodiments, the heterologous target protein may be an animal (e.g., human) protein, an insect protein, a microbial protein, or a plant protein.

In certain embodiments, the heterologous target protein is a transporter, an enzyme, a nuclear receptor, or a transcription factor.

Transporter Proteins

The methods of the invention described herein may be applied to any transporter protein (e.g., a transporter protein that is molecular therapeutic target). For example, once the transporter protein is expressed functionally in transgenic plant cells, a genetically heterogeneous population of mutant transgenic plant cells expressing the heterologous target protein (transgenic secondary plant cells) are generated and then exposed to a toxin, such as a cytotoxin (i.e., the compound), which is transported by the transporter protein. If the toxin is accumulated by the activity of the transporter, over-production of inhibitors of the transporter will then provide a survival advantage, and the population of surviving cells will be "enriched" in mutants with these characteristics. Alternatively, if the transporter removes the toxin from the cell, over-production of activators of the transporter will then provide a survival advantage, and the population of surviving cells will be "enriched" in mutants with these characteristics.

Accordingly, in certain embodiments of the invention, the heterologous target protein is a transporter protein.

In certain embodiments, the transporter protein is a dopamine transporter or a serotonin transporter.

As described herein, the compound used in the methods of the invention will be selected based on the heterologous target protein. If the heterologous target protein is a transporter, the compound that is selected would be a toxic compound (e.g., a compound that results in the cell death of non-transgenic cells at a given concentration) that is transported by the transporter either into the cell (selecting for inhibitors) or out of the cell (selecting for activators).

In certain embodiments of the invention, the mutagenized transgenic cells overproduce one or more activators of the transporter. In certain embodiments, the mutagenized transgenic cells overproduce one or more inhibitors of the transporter As described in Example 1, the human dopamine transporter protein was expressed in mutant cells of a native lobelia, *Lobelia cardinalis*, and then selected for survival using a cytotoxin, MPP+, which is accumulated intracellularly by the activity of the transporter protein. The experimental data indicate that surviving mutants are enriched in individuals which are overproducing metabolites that inhibit the dopamine transporter. These active compounds are of potential value in several conditions, for example, conditions which affect the human central nervous system, including but not limited to Parkinson's Disease, psychostimulant addiction, attention deficit disorder, attention deficit hyperactivity disorder, and depression [1-6].

Accordingly, in certain embodiments, the transporter is a dopamine transporter. In certain embodiments, the transporter is a dopamine transporter and the selected plant is a *Lobelia cardinalis* plant. In certain embodiments, the compound is a toxic compound (e.g., a cytotoxin, e.g., 6-OHDA, MPTP or MPP+). In certain embodiments, the compound is MPP+. In certain embodiments, the mutagenized transgenic cells overproduce one or more inhibitors of the dopamine transporter (e.g., lobinaline or squalene).

The methods described herein have also been performed using a rat serotonin transporter, which is expressed in cells of a native *Hypericum* species, *Hypericum punctatum*. Mutants of these cells were then selected for survival using the compound 6,7-dihydroxytryptamine, which is a cytotoxin that is accumulated intracellularly by the activity of the serotonin transporter [7]. The metabolites from this example may be used as potential treatments for major depression.

Accordingly, in certain embodiments, the transporter is a serotonin transporter (e.g., a rat serotonin transporter). In certain embodiments, the transporter is a serotonin transporter and the selected plant is a *Hypericum punctatum* plant. In certain embodiments, the compound is a toxic compound (e.g., a cytotoxin, e.g., 6,7-dihydroxytryptamine). In certain embodiments, the mutagenized transgenic cells overproduce one or more inhibitors of the serotonin transporter.

Enzyme Proteins

In certain embodiments, the heterologous target protein is an enzyme.

In certain embodiments, the enzyme is a rat alcohol dehydrogenase enzyme.

The type of compound used for selection of the mutagenized transgenic cells depends on the specific enzyme selected for the methods described herein and whether inhibitors or activators are desired. For example, if inhibitors of the enzyme are desired, the compound would be a precursor to a toxic compound, such that the activity of the enzyme would convert the precursor to a toxic compound (e.g., a cytotoxic compound). Under these conditions mutagenized transgenic cells that over-produce metabolites that decrease the activity of the enzyme (i.e., inhibitors) have a survival advantage. Thus, in certain embodiments, the compound is a precursor to a toxic compound. In certain embodiments, the mutagenized transgenic cells overproduce one or more inhibitors of the enzyme.

Conversely, if activators (or co-factors) of the enzyme are desired, the compound would be a toxic precursor, such that the activity of the enzyme would detoxify the toxic precursor. Under these conditions mutagenized transgenic cells that over-produce metabolites that increase the activity of the enzyme (i.e., activators or co-factors) have a survival advantage. Thus, in certain embodiments, the compound is a toxic precursor. In certain embodiments of the invention, the mutagenized transgenic cells overproduce one or more activators of the enzyme.

As an example of the use of an enzyme as the heterologous target protein in these methods, a rat alcohol dehydrogenase enzyme was expressed in cells of tobacco, *Nicotiana tabacum*, and a mutant population was exposed to ethanol. Ethanol is converted to the cytotoxic product, acetaldehyde, by the activity of this enzyme [8]. Surviving mutants were enriched in individuals over-producing cytoprotective metabolites, which are of potential value in alcoholic liver damage.

Accordingly, in certain embodiments, the enzyme is an alcohol dehydrogenase enzyme (e.g., from rat). In certain embodiments, the enzyme is an alcohol dehydrogenase enzyme and the selected plant is *Nicotiana tabacum*. In certain embodiments, the compound is a precursor to a toxic compound. In certain embodiments, the precursor to a toxic compound is ethanol, which is converted to acetaldehyde by the activity of the alcohol dehydrogenase enzyme.

Nuclear Receptors/Transcription Factors

In certain embodiments, the heterologous target protein is a nuclear receptor and/or a transcription factor.

In certain embodiments, the heterologous target protein is a nuclear receptor. In certain embodiments, the nuclear receptor is an estrogen receptor or a domain thereof (e.g., ligand binding domain), or a glucocorticoid receptor or a domain thereof (e.g. ligand binding domain).

In certain embodiments, the nuclear receptor is an estrogen receptor subtype beta (ERbeta) or a domain thereof (e.g., the ligand binding domain) or an estrogen receptor subtype alpha (ERalpha) or a domain thereof (e.g., the ligand binding domain).

In certain embodiments, the heterologous target protein is a transcription factor.

When the heterologous target protein is a nuclear receptor or transcription factor, its activation is linked to either cell survival or cell death, depending on whether the overproduction of activators or inhibitors are desired, respectively.

In certain embodiments, the mutagenized transgenic cells overproduce one or more activators (e.g., agonists or partial agonists) of the nuclear receptor or transcription factor. For example, if activators of the nuclear receptor/transcription factor are desired, the nuclear receptor/transcription factor is linked to the expression of a mechanism of antibiotic resistance. This linkage results in the survival of mutant cells that overproduce activators of the heterologous target protein (e.g., it favors biosynthesis of phytochemicals that act as agonists and/or partial agonists at the heterologous target protein). Thus, in certain embodiments, the activation of the nuclear receptor or transcription factor is operably linked to the expression of a selection marker (e.g., an antibiotic resistance gene). In certain embodiments, the vector comprising the gene encoding the nuclear receptor/transcription factor further comprises a selection marker, e.g., an antibiotic resistance gene.

As an example of this method, the ligand binding domain of the human estrogen receptor subtype beta (ERbeta) was expressed in cells of soybean, *Glycine max*, and activation of this protein was linked, via the estrogen responsive element, to expression of a bacterial kanamycin resistance gene. Mutant cells which survived kanamycin exposure were shown to have changed their metabolism toward increased levels of phytoestrogens which activate ERbeta. These metabolites are of potential value, for e.g., the treatment of breast cancer or as hormone replacement therapy [9, 10].

Accordingly, in certain embodiments, the nuclear receptor is ER beta or the ligand binding domain thereof. In certain embodiments, the nuclear receptor is ER beta or the ligand binding domain thereof and the selected plant is *Glycine max*. In certain embodiments, the activation of ER beta is operably linked to the expression of an antibiotic resistance gene. In certain embodiments, the vector comprising the gene encoding ER beta further comprises an antibiotic resistance gene. In certain embodiments, the vector comprising the gene encoding ER beta further comprises an antibiotic resistance gene operably linked to a hormone responsive element. In certain embodiments, the compound is an antibiotic compound that corresponds to the antibiotic resistance gene (e.g., the antibiotic is kanamycin and the antibiotic resistance gene is a kanamycin resistance gene).

Conversely, in certain embodiments, the mutagenized transgenic cells overproduce one or more inhibitors (e.g., antagonists/partial antagonists) of the nuclear receptor or transcription factor. For example, if the desired product is an inhibitor or antagonist of a nuclear receptor or transcription factor, then its activation by the compound is linked to cell death. Thus, in certain embodiments, the activation of the nuclear receptor or transcription factor is operably linked to the expression of a cell death gene. In certain embodiments, the vector comprising the gene encoding the nuclear receptor/transcription factor further comprises a cell death gene. In certain embodiments, the compound is capable of activating the nuclear receptor or transcription factor. In certain embodiments, the mutagenized transgenic cells are further exposed to a second compound, wherein the second compound causes cell death upon expression of the cell death gene (e.g., the cell death gene is dao1 and the mutagenized transgenic cells are maintained in growth medium comprising specific D-amino acids, D-valine or D-isoleucine, which are converted to toxic products by the activity of the dao 1 gene product).

As an example of this method, the ligand binding domain of human ERalpha was expressed in cells of licorice, *Glycyrrhiza glabra*, and the activation of this protein was linked, via the estrogen responsive element, to the expression of a yeast "death gene" dao1, which causes specific D-amino acids to become cytotoxic. Mutant cells which survive when exposed to estradiol (estrogen) and D-amino acids should be enriched in individuals overproducing metabolites that inhibit the activation of ERalpha. These molecules may be antagonists, or partial agonists, that functionally act as an antagonist in the presence of estradiol. These are of potential value in the pharmacotherapy of hormone-responsive breast cancer [9].

Accordingly, in certain embodiments, the nuclear receptor is ER alpha or the ligand binding domain thereof. In certain embodiments, the nuclear receptor is ER alpha or the ligand binding domain thereof and the selected plant is *Glycyrrhiza glabra*. In certain embodiments the activation of ER alpha is operably linked to the expression of a cell death gene (e.g., yeast "death gene" dao1). In certain embodiments, the vector comprising the gene encoding ER alpha further comprises a cell death gene (e.g., yeast "death gene" dao1). In certain embodiments, the vector comprising the gene encoding ER alpha further comprises a cell death gene operably linked to a hormone responsive element. In certain embodiments, the compound is capable of activating ER alpha. In certain embodiments, the mutagenized transgenic cells are exposed to a first compound and a second compound (e.g., a second composition), wherein the first compound is estradiol or estrogen and the second compound/composition comprises D-amino acids (e.g., D-valine and/or D-isoleucine).

Certain Specific Embodiments

Included below are a number of specific embodiments of the invention. The elements recited in these methods may be independently defined and/or selected from the various descriptions provided throughout the application.

Certain embodiments of the invention provide a method comprising:

a) selecting a species of plant that produces activators or inhibitors of a heterologous target protein;

b) transforming cells from the selected plant with a vector comprising a gene encoding the heterologous target protein, to obtain transgenic primary plant cells;

c) obtaining an explant from the transgenic primary plant cells;

d) mutagenizing the explant to form mutagenized transgenic cells; and e) exposing the mutagenized transgenic cells to a compound, wherein mutagenized transgenic cells that overproduce one or more activators or inhibitors of the heterologous target protein, as compared to a non-mutant transgenic plant cell from the same species, survive; and wherein mutagenized transgenic cells that do not overproduce one or more activators or inhibitors of the heterologous target protein, as compared to a non-mutant transgenic plant cell from the same species, die.

Certain embodiments of the invention provide a method comprising:

a) selecting a species of plant that produces activators or inhibitors of a heterologous target protein;

b) infecting cells (e.g., a seedling) from the selected plant species with *Agrobacterium rhizogenes* comprising a vector comprising a gene encoding the heterologous target protein, to obtain a transgenic primary hairy root;

c) obtaining an explant from the transgenic primary hairy root;

d) infecting the cells from the explant with *Agrobacterium rhizogenes* comprising an activation tagging mutagenesis (ATM) vector, to obtain a mutagenized transgenic secondary hairy root; and e) exposing the mutagenized transgenic secondary hairy root to a compound, wherein mutagenized transgenic secondary hairy roots that overproduce an activator or inhibitor of the heterologous target protein, as compared to a non-mutant transgenic hairy root, survive; and wherein mutagenized transgenic secondary hairy roots that do not overproduce an activator or inhibitor of the heterologous target protein, as compared to a non-mutant transgenic hairy root, die.

Certain embodiments of the invention provide a method comprising:

a) selecting a species of plant that produces activators or inhibitors of a first heterologous target protein and a second heterologous target protein;

b) transforming cells from the selected plant with a vector comprising a gene encoding the first heterologous target protein, to obtain transgenic primary plant cells;

c) transforming cells from an explant obtained from the primary transgenic plant cells with a vector comprising a gene encoding the second heterologous target protein, to obtain transgenic secondary plant cells;

d) mutagenizing cells from an explant obtained from the transgenic secondary plant cells to form mutagenized transgenic cells;

e) exposing the mutagenized transgenic cells to a first compound and a second compound, wherein mutagenized transgenic cells that overproduce one or more activators or inhibitors of the first heterologous target protein and one or more activators or inhibitors of the second heterologous target protein, as compared to a non-mutant transgenic plant cell from the same species, survive; and wherein mutagenized transgenic cells that do not overproduce one or more activators or inhibitors of the first heterologous target protein and one or more activators or inhibitors of the second heterologous target protein, as compared to a non-mutant transgenic plant cell from the same species, die.

Differential Target-Directed Biosynthesis of Plant Metabolites

The methods described above may be extended to direct the metabolism of a plant species toward highly-subtype selective activators of a heterologous target protein. This requires the co-expression of two heterologous target proteins, one linked to plant cell survival and one linked to cell death. This generates intense pressure to direct production of metabolites toward one heterologous target and away from the other heterologous target protein.

In the differential target directed biosynthesis methods described herein, the two heterologous target proteins may be any combination of transporters, enzymes, nuclear receptors or transcription factors (e.g., as described above), and activity at each selected for as described in the above methods that utilizing a single heterologous target protein. For example, if a plant species contained a metabolite or metabolites with desirable inhibitory activity at a transporter protein, but undesirable inhibitory activity on an enzyme then both heterologous proteins would be expressed in the plant cell with the transporter activity linked to a mechanism of cell death (accumulation of a toxic compound for example) and the enzyme linked to a mechanism of cell survival (detoxification of a toxic precursor). Exposure of these transgenic cells to both the toxic compound and the toxic precursor would favor the survival of mutants which overproduce inhibitors of the transporter (the desirable activity) but which produce less of the metabolite with the undesirable activity (inhibition of the enzyme). The two target proteins could also be of the same class, for example the two subtypes of estrogen receptor ERalpha and ERbeta as described below.

Accordingly, certain embodiments of the invention provide a method comprising:

a) selecting a species of plant that produces activators of a first heterologous target protein and a second heterologous target protein;

b) transforming cells from the selected plant with a first vector comprising a gene encoding the first heterologous target protein and a gene encoding a selection marker, wherein the activation of the first heterologous target protein is operably linked to the expression of the selection marker, to obtain transgenic primary plant cells;

c) transforming cells from an explant obtained from the transgenic primary plant cells with a second vector comprising a gene encoding the second heterologous target protein and a cell death gene, wherein activation of the second heterologous target protein is operably linked to the expression of the cell death gene, to obtain transgenic secondary plant cells;

d) mutagenizing cells from an explant obtained from the transgenic secondary plant cells to form mutagenized transgenic cells; and e) exposing the mutagenized transgenic cells to a first compound and a second compound, wherein the first compound causes cell death in the absence of the selection marker expression, wherein the second compound causes cell death when the cell death gene is expressed, wherein the mutagenized transgenic cells that overproduce one or more activators of the first heterologous target protein, which are not activators of the second heterologous target protein, survive; wherein overproduction is compared to a non-mutant transgenic plant cell from the same species; and wherein all other cells die.

In certain embodiments, the mutagenized transgenic cells are exposed to the first compound and second compound sequentially. In certain embodiments, the mutagenized transgenic cells are exposed to the first compound and second compound simultaneously.

The elements recited in the above methods may be independently defined and/or selected from the various descriptions provided throughout the application. For example, the first and second heterologous target proteins may be independently selected from the lists of heterologous target proteins provided above.

For example, co-expression of ER beta, wherein activation of this protein is linked to antibiotic resistance, and ER alpha, wherein activation of this protein is linked to cell death on exposure to specific D-amino acids, would drive metabolism of the species toward highly selective agonists of ERbeta and away from metabolites which activate ERalpha (differential target-directed biosynthesis) (see, Example 2). This would be of value in the, e.g., treatment and/or prevention of hormone-responsive breast cancer.

Accordingly, in certain embodiments of the invention, the first heterologous target protein is ERbeta and the second protein is ERalpha.

In certain embodiments, the first vector comprises a gene encoding ERbeta and a gene encoding a selection marker (e.g., an antibiotic resistance gene), wherein the activation of ERbeta is operably linked to the expression of the selection marker. The first compound is chosen based on the type of selection marker in the vector, wherein a compound that causes cell death in the absence of the selection marker expression is chosen. For example, if the selection marker is an antibiotic resistance gene, the compound would be a corresponding antibiotic (e.g., the first compound is kanamycin and the selection marker is a kanamycin resistance gene).

In certain embodiments, the second vector comprises a gene encoding ERalpha and a cell death gene (e.g., yeast dao1), wherein the activation of ERalpha is operably linked to the expression of the cell death gene. The second compound is chosen based on the type of cell death gene, wherein a compound that causes cell death when the cell death gene is expressed is chosen. For example, if the cell death gene is dao1, the compound would be D-amino acids (e.g., D-valine and D-isoleucine).

Compositions and Methods of Use Thereof

Plant Cells, Extracts Thereof and Metabolites

Certain embodiments of the invention provide a transgenic plant cell, cell line or plant prepared by the methods described herein. For example, these plant cells may be propagated (e.g., regenerated into a plant) and used for compound discovery or for the production of known or novel active metabolites.

Certain embodiments of the invention provide an extract prepared from a plant cell, cell line or plant described herein. For example, in certain embodiments, the extract is a crude extract (e.g., has been minimally processed).

In certain embodiments, the extract comprises lobinaline and/or squalene. For example, in certain embodiments the extract comprising lobinaline and/or squalene is prepared from a plant cell prepared by the methods described herein, wherein the heterologous target protein is a dopamine transporter, the selected plant species is *L. cardinalis* and the compound is MPP+.

Certain embodiments of the invention provide a metabolite (e.g., an activator or an inhibitor of a heterologous target protein) prepared from a plant cell, cell line or plant described herein. Metabolites may be isolated from plant cells using techniques known in the art (see, e.g., Example 1).

The invention also provides a pharmaceutical composition comprising an extract or metabolite as described herein or a pharmaceutically acceptable salt thereof, and a pharmaceutically acceptable excipient.

The invention also provides processes and intermediates disclosed herein that are useful for preparing plant metabolites (i.e., activators and inhibitors of heterologous target proteins) and extracts.

As described in Example 1, the plant metabolite lobinaline was identified as having pharmacological activity at nicotinic receptors for acetylcholine and as an inhibitor of the dopamine transporter. Accordingly, certain embodiments of the invention provide a method for inhibiting a dopamine transporter, comprising contacting a cell (e.g., a mammalian cell, e.g., a human cell) in vivo or in vitro with lobinaline. Certain embodiments also provide a method for modulating the activity of a nicotinic receptor for acetylcholine, comprising contacting a cell (e.g., a mammalian cell, e.g., a human cell) in vivo or in vitro with lobinaline.

The invention also provides a method for treating or preventing a disease or disorder in an animal (e.g., a mammal such as a human) comprising administering an extract comprising lobinaline to the animal.

The invention also provides a method for treating or preventing a disease or disorder in an animal (e.g., a mammal such as a human) comprising administering lobinaline or a pharmaceutically acceptable salt thereof to the animal.

The invention also provides lobinaline or a pharmaceutically acceptable salt thereof for the prophylactic or therapeutic treatment of a disease or disorder in an animal (e.g., a mammal such as a human).

The invention also provides the use of lobinaline or a pharmaceutically acceptable salt thereof to prepare a medicament for treating a disease or disorder in an animal (e.g. a mammal such as a human).

In certain embodiments, the disease or disorder is Parkinson's disease, drug dependence (e.g., alcoholism or drug dependence, including psychostimulant addition), attention deficit disorder, attention deficit hyperactivity disorder or depression.

The invention also provides a lobinaline or a pharmaceutically acceptable salt thereof for use in medical therapy.

Administration

The plant metabolites (e.g., lobinaline) described herein, for example in purified form or as extracts, can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds (i.e., the plant metabolites, such as lobinaline) may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.01% of active compound. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound, in the form of a purified metabolite, may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes, microspheres or nanoparticles. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In case of sterile preparations or solutions, the preferred methods of preparation of the active compound powders are the vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In one embodiment, the invention provides a composition comprising a compound described herein formulated in a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Additionally, the plant extracts described herein may also be administered to a mammalian host, such as a human patient in a variety of forms adapted to the chosen route of administration, such as orally or topically, as described above for active compounds.

Methods for the Transformation of Hairy Roots

Described herein are methods for the use of *A. rhizogenes* to further transform an already transformed line of hairy roots (e.g., a *L. cardinalis* or *Glycyrrhiza glabra* hairy root). These methods are valuable as a means of introducing two or more foreign genes into a plant species, as they greatly accelerate the rate at which one can obtain a mutant with a genotype, and resulting phenotype, of interest when more than one transformation event is necessary. This circumvents the need for regeneration after each transformation, which adds considerable time when multiple transformation events are needed. It also enables one to perform repeated rounds of mutagenesis until a genotype and resulting phenotype are achieved. Lastly, this technology enables the expression of multiple foreign genes by sequential transformation of hairy roots in plant species for which a regeneration protocol does not exist and/or is not possible. As described in Example 1, these methods led to a dramatic reduction in the time needed to achieve mutants with a pharmacologically optimized phenotype and similar approaches could easily be extended, e.g., for agrochemicals and nutraceuticals.

Accordingly, certain embodiments of the invention provide a method comprising:

a) transforming plant cells comprising infecting the cells with *Agrobacterium rhizogenes* comprising a first vector comprising a first gene, to obtain a transgenic primary hairy root;

b) obtaining an explant from the transgenic primary hairy root; and c) transforming the explant cells comprising infecting the cells with *Agrobacterium rhizogenes* comprising a second vector comprising a second gene, to obtain a transgenic secondary hairy root.

In certain embodiments, plant seedlings are used for the transformation in step a) (e.g., 4-6 week old seedlings). In certain embodiments, only a portion of the plant is used for the transformation in step a). For example, in certain embodiments, hypocotyl segments from plant seedlings are used for the transformation in step a).

In certain embodiments, the first vector and/or second vector further comprises a promoter operably linked to the gene (e.g., a promoter that is functional in the plant species, e.g., the CaMV 35S promoter). In certain embodiments, the vector is an *Agrobacterium* binary vector. In certain embodiments, the vector is pCambia1301. In certain embodiments, the first vector and/or the second vector further comprises a selection marker (e.g., an antibiotic resistance gene).

In certain embodiments, the methods further comprise introducing the first vector or second vector comprising the first or second gene into the Agrobacteria.

As described herein, the methods comprise obtaining an explant from the transgenic primary hairy root. In certain embodiments, the explants are 0.5-5 cm or 1.5-2 cm in length.

In certain embodiments, the plant cells (e.g., plant seedlings) or explants from the transgenic primary hairy roots are wounded multiple times (e.g., 2, 3, 4 or more times) while in a solution of *A. rhizogenes* carrying the either the first vector or the second vector to generate the transgenic hairy roots.

In certain embodiments, the *A. rhizogenes* strain is R1000, AR1000, A4 or K599. In certain embodiments, the *A. rhizogenes* strain is AR1000, A4 or K599.

In certain embodiments, the methods further comprise maintaining the transgenic hairy roots (primary or secondary) on a plant growth medium comprising a selection agent, which corresponds to a selection marker in the vector (e.g., an antibiotic). In certain embodiments, the hairy roots are maintained on plant growth medium that does not comprise a selection marker for a period of time after infection (e.g., 6 hrs, 12 hrs, 1 day, 2 days, 3 days, 4 days or more) to allow the transformation event to transpire, and then are transferred to a plant growth medium comprising the selection agent.

In certain embodiments, the methods further comprise:

e) obtaining a second explant from the transgenic secondary hairy root; and d) transforming cells from the second explant, comprising infecting the cells with *Agrobacterium rhizogenes* comprising a third vector comprising a gene, to obtain a transgenic tertiary hairy root.

In certain embodiments, the methods may comprise further sequential transformations, wherein explants are obtained from the previously transformed hairy roots and the cells from that explant are transformed by infecting the cells with *Agrobacterium rhizogenes* comprising, e.g., a fourth, fifth, sixth, seventh, eighth, ninth, tenth, etc., vector comprising a gene, to obtain a corresponding, e.g., quaternary hairy root, transgenic quinary hairy root, transgenic senary hairy root, transgenic septenary hairy root, trangenic octonary hairy root, transgenic nonary hairy root, transgenic denary hairy root, etc.

Methods for the Detection and Quantification of Foreign Proteins in Plant Cells

As described herein a radioligand may be used to confirm and/or quantify the presence of a transgenic protein expressed in plant cells (see, Example 1).

Accordingly, certain embodiments of the invention provide a method for the detection of a transgenic protein comprising contacting a transgenic plant cell with a radio-labeled ligand, wherein the ligand is a selective ligand for the transgenic protein.

In certain embodiments, the methods further comprise detecting the radio-labeled ligand.

Certain embodiments of the invention provide a method of quantifying a transgenic protein comprising contacting a transgenic plant cell with a radio-labeled ligand, wherein the ligand is a selective ligand for the transgenic protein.

In certain embodiments, the methods further comprise quantifying the radio-labeled ligand.

As described herein, the method may be used for the detection or quantification of any transgenic protein with a corresponding selective ligand. Additionally, this method may be performed using transgenic cells from any species of plant from which a membrane preparation can be obtained.

In certain embodiments, the transgenic protein is a dopamine transporter or an estrogen receptor or domain thereof.

In certain embodiments, the transgenic plant cells are *L cardinalis, Glycyrrhiza glabra* or *Glycine max* cells.

In certain embodiments, the transgenic plant cells are *L cardinalis* cells.

General Terminology

As used herein, the term "therapeutic" or "therapeutic compound" or "therapeutic metabolite" or "therapeutic extract" refers to any agent or composition that has a beneficial effect on a mammalian recipient. Thus, these terms embraces both therapeutic and prophylactic molecules.

"Treating" as used herein refers to ameliorating at least one symptom of, curing and/or preventing the development of a given disease or condition "Synthetic" polynucleotides are those prepared by chemical synthesis. The polynucleotides may also be produced by recombinant nucleic acid methods. "Recombinant nucleic molecule" is a combination of nucleic sequences that are joined together using recombinant nucleic technology and procedures used to join together nucleic sequences known in the art.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

The terms "heterologous DNA sequence," "exogenous DNA segment" or "heterologous nucleic acid," each refer to a sequence that originates from a source foreign to the particular host cell or, if from the same source, is modified from its original form. Similarly, a "heterologous protein" or "heterologous protein domain" each refer to a protein or peptide that that originates from a source foreign to the particular host cell, or if from the same source, is modified from its original form.

By "fragment" or "portion" is meant a full length or less than full length of the nucleotide sequence.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5M, more preferably about 0.01 to 1.0M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20× SSC=3.0M NaCl/0.3 M trisodium citrate) at 50 to 55° C. Exemplary moderate stringency conditions include hybridization in 40 to 45% formamide, 1.0M NaCl, 1% SDS at 37° C., and a wash in 0.5× to 1×SSC at 55 to 60° C.

"Recombinant DNA molecule" is a combination of DNA sequences that are joined together using recombinant DNA technology and procedures used to join together DNA sequences as described, for example, in Sambrook and Russell (2001).

To confirm the presence of a recombinant DNA sequence in a host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify heterologous target proteins.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

"Operably-linked" refers to the association of molecules so that the function of one is affected by the other. For example, operably-linked nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Operably-linked" also refers to the association of peptides. For example, two protein may be operably linked if the function of one protein causes the other protein to be expressed.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"As used herein, the term "derived" or "directed to" with respect to a nucleotide molecule means that the molecule has complementary sequence identity to a particular molecule of interest.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

A vector as described herein may comprise at least one promoter and at least one gene of interest. Additionally, the vector may also include a selection gene, for example, a resistance gene (e.g., an antibiotic resistance gene), for facilitating selection of cells that have been transformed with the expression vector.

In certain embodiments, a cell may be transformed with two or more expression vectors, as least one vector comprising the gene of interest and the other containing the selection gene. The selection of a suitable promoter, enhancer, selection gene, and/or signal sequence is deemed to be within the scope of one of ordinary skill in the art without undue experimentation.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. The promoter to drive expression of the protein or the sequence encoding another agent to be delivered can be any desired promoter, selected by known considerations, such as the level of expression of a nucleic acid functionally linked to the promoter and the cell type in which the vector is to be used. Promoters can be an exogenous or an endogenous promoter. The expression of the nucleotide sequence may be under the control of a constitutive promoter or of an inducible promoter that initiates transcription only when the host cell is exposed to some particular external stimulus. In the case of a multicellular organism, the promoter can also be specific to a particular tissue or organ or stage of development. Examples include, but are not limited to, the 35 S promoter.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Expression" refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein.

The term "amino acid" includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in Dextrorotary or Levorotary stereoisomeric forms, as well as unnatural amino acids (e.g., phosphoserine, phosphothreonine, phosphotyrosine, hydroxyproline, and gamma-carboxyglutamate; hippuric acid, octahydroindole-2-carboxylic acid, statine, 1,2,3,4,-tetrahydroisoquinoline-3-carboxylic acid, penicillamine, ornithine, citrulline, alpha-methyl-alanine, para-benzoylphenylalanine, phenylglycine, propargylglycine, sarcosine, and tert-butylglycine). The term also comprises natural and unnatural amino acids (Dextrorotary and Levorotary stereoisomers) bearing a conventional amino protecting group (e.g. acetyl or benzyloxycarbonyl), as well as natural and unnatural amino acids protected at the carboxy terminus (e.g., as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc, and documents cited therein).

The terms "protein," "peptide" and "polypeptide" are used interchangeably herein.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

The invention will now be illustrated by the following non-limiting Examples.

Example 1

Abstract

When bioactive metabolites in plants are too complex for chemical synthesis, this limits their potential uses. For example, low yields of potential pharmaceuticals in plants limit production, and the synthesis of compound libraries for screening against target proteins is difficult. As described herein, an alternative is to use the genomic/biosynthetic capacity of the plant species. First, the therapeutic target protein is expressed in transgenic plant cells so that metabolites which interact appropriately with the target protein confer a survival advantage. In a gain-of-function mutant population those mutants which survive should be enriched in individuals over-producing the known "wild-type" active metabolite, or other unknown metabolites which are active at the target protein. An example is a native *Lobelia* species containing a previously uninvestigated alkaloidal inhibitor of the dopamine transporter (DAT), a target in Parkinson's Disease. Expression of the human (h)DAT in hairy root cultures of this species made these sensitive to MPP+, a cytotoxin which is accumulated intracellularly via the hDAT. Activation tagging mutagenesis was then used to generate mutant hairy roots from the transgenic hDAT line under continuous selection in MPP+. 120 MPP+-resistant mutant hairy roots were analyzed after 4 months on selection followed by two months off selection. As predicted, a large proportion show DAT inhibition well above wild-type cultures. Most of these are over-producing the major known active alkaloid, but, in several mutants, high levels of DAT inhibition do not correlate with this alkaloid, and previously undetected metabolites are present. This approach simply substitutes target-directed biosynthesis for the target-directed chemical synthesis of the pharmaceutical industry and may provide a novel technology for plant drug discovery.

*Lobelia cardinalis* Cell Cultures Expressing the Human Dopamine Transporter Protein An initial step of the methods described herein is the identification of a plant species for the target-directed biosynthesis of metabolites. This example describes the biosynthesis of metabolites with inhibitory effects on the dopamine transporter. Thus, a plant species, which contains previously uninvestigated metabolites with inhibitory effects on the dopamine transporter, was first identified. This activity is relatively common in plants, probably because these metabolites have evolved as "anti-feedants" targeted on the dopamine transporter in the central nervous system of herbivorous insects.

Increased dopamine signaling is also involved in aversive learning, as it is associated with aversive stimuli in insects [11]. Once such a species had been identified, the human dopamine transporter protein was expressed in cells of this species and was shown to be functional. A genetically heterogeneous mutant population of these transgenic cells was then selected for survival using a toxin transported into cells by the dopamine transporter. Mutations which result in increased biosynthesis of metabolites, which inhibit the transporter, conferred a survival advantage on cells subjected to selection in the presence of cytotoxic substrates of the transporter. Extracts of the toxin-resistant mutant population were then analyzed and compared with control populations for inhibitory activity at the dopamine transporter, and for the presence of metabolites known to be active at the transporter. It was shown that the toxin-resistant population was enriched in cells/cultures that over-produced metabolites that inhibited the dopamine transporter. As described herein, the inhibitory activity may reside either in metabolites known to be active from the wild-type plant, or active metabolites which are not detectable in the wild-type plant.

Choice of Plant Species

As described herein, the original aim was to seek neuroprotective metabolites which act as agonists at the alpha7 subtype of the nicotinic receptor for acetylcholine (alpha7nicAChR) and also inhibit the dopamine transporter (DAT). These mechanisms together should provide a therapeutic advantage in Parkinson's Disease [1, 2, 12] and in some types of drug dependence (e.g. alcoholism and nicotine dependence [13, 14]). Additionally, certain classes of inhibitory modulators of the dopamine transporter have demonstrated the ability to decrease self-administration of psychostimulants, such as cocaine and methamphetamine, without affecting seeking for natural rewards and/or reinforcers (food, etc.) [3, 15, 16]. DAT inhibitors with these characteristics represent therapeutically valuable leads for the development of pharmacotherapies for psychostimulant abuse [3, 15, 16]. An extract library of ~1000 native plant species was first screened (using radioligand binding) for pharmacological activity at nicAChRs with relative selectivity for the alpha7 subtype. 10 species were chosen for further study based on relative displacement of radioligands with selectivity for alpha7 nicAChRs or alpha4/beta2 nicAChRs (these are the two major subtypes in mammalian brain) [17-19]. Only *Lobelia cardinalis* extracts also contained inhibitory activity on the uptake of [$^3$H]-dopamine into rat brain striatal synaptosomes (an assay for inhibition of the dopamine transporter). These activities have not previously been reported in extracts of this species, and it is not a commonly known medicinal plant. *L. cardinalis* was therefore used for proof of concept in the following experiments.

Major Active Metabolite in *L. cardinalis*

Assay-guided analysis (nicAChR radioligand binding and [$^3$H]-dopamine uptake) of preparative HPLC fractions identified a single area of the chromatogram containing the major part of both activities. Further chromatographic separation and pharmacological analysis identified a fraction containing a single major alkaloid. GC/MS analysis identified this as the binitrogenous decahydroquinolone alkaloid, lobinaline. This has previously been described as the major alkaloid in *L. cardinalis* [20, 21], but its activities at nicAChRs and the dopamine transporter have not previously been investigated. The alkaloid is complex (5 chiral centers) and there is no published synthesis. This conventional separation therefore identified lobinaline as probably the cause of most of the relevant activity in the plant extract; however, other more active compounds may also be present. It is likely that there are several other active metabolites, present at lower concentrations, that may be more or less active than lobinaline.

Pharmacological Activity of Purified Lobinaline

Lobinaline was purified from a methanol extract prepared from dried aerial portions of *L. cardinalis*. The methanolic extract was dried under vacuum, resuspended in water, and defatted with hexane. The hexane phase was removed, and the remaining aqueous phase was partitioned with chloroform. The chloroform phase was collected, dried under vacuum, and lobinaline was purified from this fraction by acid/base extraction to yield lobinaline of ~95% purity (single peak and spectroscopic authenticity by GC-MS). This compound was then dissolved in DMSO and used in aqueous solution to evaluate its effects on the dopamine transporter and nicAChRs, both in rat brain preparations and in the human dopaminergic neuroblastoma cell line SH-SY5Y. Antioxidant activity of lobinaline was evaluated using the dipheny picryl hydrazyl free radical scavenging assay.

(a) nicAChR Binding:

lobinaline inhibits [$^3$H]-epibatidine binding (non-subtype selective) with $K_i$=17.26 µM, and inhibits [$^3$H]-MLA binding (alpha7 selective ligand) with a Ki=104.8 µM. It is therefore relatively non-selective, whereas almost all known plant alkaloids are relatively selective for the alpha4/beta7 nicAChR.

(b) Dopamine Transporter (DAT) Inhibition:

[$^3$H]-dopamine uptake in rat striatal synaptosomes was inhibited by lobinaline ($IC_{50}$=12 µM, significantly below that of lobeline [22]). Lobinaline also completely inhibited [$^3$H]-GBR12935 specific binding to rat striatal membranes, but with a $K_i$ of 89 µM. The low affinity binding of lobinaline to this site on the DAT may therefore not be directly related to its functional effect. Lobinaline also inhibits the toxicity of MPP+ (a cytotoxic substrate for the dopamine transporter [1, 23]) on SH-SY5Y cells (~100 µM). It also inhibits NMDA-induced toxicity on these cells at similar concentrations, consistent with its activity at nicAChRs (which can lead to desensitization of glutamate/NMDA receptors).

(c) Free Radical Scavenging:

Stable free radical diphenyl picryl hydrazyl (DPPH) scavenging was used to assess anti-oxidant activity. Lobinaline inhibits DPPH free radical activity, with an $IC_{50}$ of 21.1 µM. The plant flavonoid quercetin, which is known to be a potent anti-oxidant, was evaluated for comparison, and was found to have an $IC_{50}$ of 11.2 µM in this assay.

(d) Effects on [$^3$H]-Dopamine (DA) Release from Stiatal Slices:

A lobinaline-containing fraction (chloroform fraction; see above) from *L. cardinalis* caused a rapid concentration-dependent release of [3H] from rat brain slices preloaded with [$^3$H]-DA (in the presence nomifensine and pargyline, a DAT inhibitor and monoamine oxidase inhibitor, respectively). The initial phase of [3H] release was almost completely inhibited by 10 µM mecamylamine, indicating agonist activity at nicAChRs. However, the same concentration of lobinaline reduced the DA release induced by 10 µM nicotine, supporting the previous indication of partial agonist activity at nicAChRs.

(e) Pharmacokinetics (PK) and Toxicology of Lobinaline:

the literature [20] indicates appropriate PK and low mammalian toxicity ($LD_{50}$ reported for lobinaline was less than that of lobeline in mice), and the Lipinski data from PubChem support its potential as a lead compound (M.W.=386, Hydrogen Bond Donors=0, Hydrogen Bond Acceptors=2, Log P=4.8, Molar fractivity=82.47).

All of these actions confirm that lobinaline is a potential natural lead compound for pharmaceutical development. However, its complexity and lack of a method for chemical synthesis preclude its evaluation by conventional means because neither the compound itself, nor a related compound library can be generated by chemical synthesis. This makes *Lobelia cardinalis* and lobinaline ideal candidates for proof of concept for target-directed biosynthesis in mutant cell cultures.

Development of Cell Culture System for *L. cardinalis*

Hairy Root Transformation:

methods for *Lobelia erinus* [24] were modified to develop an efficient protocol for *Agrobacterium rhizogenes*-mediated hairy root induction in *L. cardinalis*. Briefly, hypocotyl segments from 4-6 week old in-vitro grown *L. cardinalis* seedlings were used as target explants, wounded 3-4 times with a sterile hypodermic needle, and soaked in a solution of *A. rhizogenes* strain AR1000 carrying the binary vector pCambia1301, which carries the a GUS reporter gene under control of the constitutively active CaMV 35S promoter. Transgenic hairy roots emerged from 53% of hypocotyl explants after 4-6 weeks, with an average of 3 transgenic hairy roots per explant. Successful transformation of hairy roots was confirmed using the GUS histochemical staining assay, as described previously [25]. Explants consisting of root apices (1.5-2 cm in length) were transformed by *A. rhizogenes* R1000 carrying binary vector pKM24GFP. 25-55 hairy roots can be produced from one explant with >17% of these both GUS+ and GFP+. This validates first generating transgenic primary hairy roots (1°HRs), and then sequentially transforming them to generate mutant secondary hairy roots (2°HRs) (i.e., two or more foreign genes may be introduced into a plant species using this method). This approach greatly accelerates the rate at which one can obtain a mutant with a genotype, and resulting phenotype, of interest when more than one transformation event is necessary. This circumvents the need for regeneration after each transformation, which adds considerable time when multiple transformation events are needed. It also enables one to perform repeated rounds of mutagenesis until a genotype, and resulting phenotype, is achieved. Lastly, this technology enables the expression of multiple foreign genes by sequential transformation of hairy roots in plant species for which a regeneration protocol does not exist and/or is not possible. As described below, using this method for the instant experiments led to a dramatic reduction in the time needed to achieve mutants with a pharmacologically optimized phenotype, as it was possible to by-pass regeneration of transgenic hDAT plants and avoid the potential for masking the foreign gene.

As described herein, all subsequent studies used the same clonal line of transgenic hDAT hairy roots. Additionally, hairy root cultures of *L. cardinalis* (generated and/or transformed by *A. rhizogenes* infection) were used for all the subsequent experiments on target-directed biosynthesis.

Functional Expression of the Human Dopamine Transporter (hDAT) in Plant Cells (a). Cloning the hDAT Gene.

The full-length cDNA of human DAT (1.8 kb) was PCR-amplified and cloned into pGEM-T Easy vector system (Promega), sequenced, and authenticity confirmed. The full-length hDAT cDNA was sub-cloned into pKYLX80 vector using EcoR1-Xba1 restriction enzymes. After digestion with these enzymes, the hDAT gene was restricted out from the pKYLX80 vector with the 35S promoter, and then this cassette ligated into a modified pCambia1301. This construct was then mobilized into *A. rhizogenes* strain R1000, and used to infect *L cardinalis* seedlings to obtain transformed 1°HRs expressing the hDAT gene.

(b). Presence of hDAT Gene in Transgenic *L. cardinalis* Hairy Roots:

1 ug total RNA from each culture was reversely transcribed and amplified using a cDNA synthesis kit (Invitrogen). The PCR products were run in agarose gel-based electrophoresis and stained with ethidium bromide, then analyzed under UV light (Gel-Doc). A 1.8 kb amplified product confirmed hDAT expression. Non-transformed HRs were negative.

(c). Presence of hDAT Protein in Transgenic *L. cardinalis* Hairy Roots:

commercially available antibodies showed a band at the predicted position, but with cross reaction to multiple other proteins. [$^3$H]-GBR12935, a highly selective radioligand for the DAT [3] bound to transgenic hDAT hairy root cultures with saturable specific, 1 site binding (Graphpad). Kd 7.33 nM and Bmax=1.04+0.9 pmol/mg membrane protein were within ranges for mammalian CNS tissue [3]. There was no specific binding to non-transgenic control hairy roots.

(d) Functionality of the hDAT in Transgenic *L cardinalis* Hairy Roots:

HRs were incubated in buffer containing [3H]DA for 1-30 min at 37° C. (non-specific uptake at 0° C.). Roots were ground and extracted with buffer containing 1500 units/ml cellulase for 24 hr. Significantly higher CPM were found in lysates from hDAT-transfected hairy roots (~3× greater rate of uptake in controls). The DAT selective inhibitor GBR12909 (100 μM) [3] completely removed this effect as did Na+ free buffer (the hDAT functions as a "sodium symporter").

(e) Toxicity of DA-Ergic Toxins in *L cardinalis* Hairy Roots:

toxicity was induced by exposure to 6-OHDA (50 uM), MPTP (100 μM) or MPP+ (100 μM), (threshold toxic concentrations in non-transgenic cultures). Trypan blue staining for toxicity was quantified using ImageJ software. Non-transgenic 1°HRs were not significantly damaged, but 24 h toxin-exposure was lethal to ~50% of cells in transgenic hDAT 1°HRs. Cytotoxicity was inhibited by the selective DAT inhibitor GBR12909 [3], but this was less effective in inhibiting toxicity due to 6-OHDA (which may produce some toxicity independent of the DAT [26]). Furthermore the use of MPP+, rather than MPTP, leads to a selection process that is more selective for mutants overproducing ligands which inhibit the hDAT. Since MPTP is converted to the its cytotoxic metabolite, MPP+, by oxidases [1, 23], biosynthesis of oxidase inhibitors would also confer a survival advantage if MPTP were chosen as a selection agent (monoamine oxidase inhibitors prevent MPTP toxicity in SH-SY5Y neuroblastoma cells [27]). Based on the data, MPP+ was chosen as the toxin for *L. cardinalis* hairy root/hDAT selection, with the prediction that overproduction of endogenous inhibitors of the hDAT should increase survival of individual mutants.

Generation of an MPP+-Resistant Mutant Transgenic Population

Rationale:

Conventionally, for selection, a large population of mutants would first be generated and then be exposed to a toxin concentration which is lethal to non-mutants. This requires the generation and maintenance of very large populations. As described herein, an alternative is to generate the mutants under selection pressure. In this approach a concentration of toxin is chosen which prevents the survival and/or growth of the great majority of mutants. Now, only transformed transgenic plant cells expressing the target protein in which a mutation has caused a resistant phenotype will develop into a secondary hairy root (2°HR). This is more efficient because only small numbers of resistant mutants are generated and maintained.

Methods for Selection:

Activation tagging mutagenesis (ATM) was performed on 1.5-2 cm explants taken from 1°HRs that functionally express hDAT, to generate a heterogeneous population of 2°HRs possessing gain-of-function mutations and a functional hDAT. Explants were wounded with a sterile hypodermic needle 3-4 times while in a solution of *A. rhizogenes* AR1000 carrying the ATM vector PCVICEn4HPT [28]. Explants were soaked in the solution 30 minutes thereafter, placed in the dark on antibiotic free plant growth medium for 3 days to allow the transformation event to take place, and then transferred to plant growth medium containing antibiotic. Small nodules begin emerging from 1°HRs at wound sites within ~2 weeks, each representing the initiation of a 2°HR. Immediately upon seeing the formation of such nodules, explants were transferred to selection medium (plant growth medium containing antibiotics and 100 µM MPP+, so that only cells with mutations conferring MPP+ resistance should develop into mature 2°HRs. Mutant cultures are maintained on plant growth medium containing MPP+ for 4 months to ensure stability of the resistant phenotype. They are then removed and placed on plant growth medium lacking MPP+ for 2 months before screening extracts, to ensure that residual MPP+ will not interfere with the analysis (at this stage MPP+ is undetectable in all these cultures). Each explant from 1°HRs expressing the hDAT that is activation tagged produces a minimum of 20 2°HRs in the absence of selection. To date, 1700 1°µHRs have been activation tagged, representing at least 34,000 2°HRs predicted to have developed. The rate of successful sequential transformations was ~17%, which equates to 5,780 2°HRs with gain-of-function mutations and a functional hDAT. Under MPP+ selection only 120 2°HRs (0.35%) have survived and developed. This MPP+-resistant population of 2°HRs was then compared with non-selected activation tagged mutants that functionally expressed the hDAT and control groups to establish the pharmacological and chemical characteristics of each population.

Screening of Selected and Non-Selected Populations:

Rationale:

resistance to MPP+ toxicity may be via many different mechanisms including artifacts. For example, transgene silencing, or knock-out by ATM, would prevent MPP+ accumulation. Based on prior studies these are very rare occurrences. Some other mechanisms for MPP+ resistance should be detectable in extracts. For example, increased antioxidant production would prevent oxidative damage induced by MPP+, as an alternative to the overproduction of DAT inhibitors. Since lobinaline is an excellent anti-oxidant (see above), over-production of this metabolite (or similar compounds) would protect via inhibition of oxidative damage, and by inhibition of MPP+ accumulation. Either or both of these mechanisms are of potential therapeutic value. Therefore individual culture extracts were screened for anti-oxidant activity, as well as for inhibition of DAT-mediated [$^3$H]-DA uptake. The prediction is that the MPP+-resistant population will be "enriched" in individuals with these characteristics.

Methods and Results:

Dried methanolic extracts prepared from individual *L. cardinalis* hairy roots were dissolved in assay buffer and tested for (a) concentration-dependent effects on [$^3$H]-DA uptake into rat striatal synaptosomes, (b) quenching stable DPPH radical, as measured by absorbance at 517 nm. The results are presented as "lobinaline equivalents" calculated from pure lobinaline concentration response curves (FIG. 1). FIG. 1 is a scattergram comparing the inhibition of [$^3$H]-DA uptake caused by extracts from individual hairy root cultures from four populations (note: each circle on the scattergram represents the activity of an extract prepared from a single hairy root culture). The DAT- population is control 1°HRs which have been transformed with *A. rhizogenes*, but without the hDAT construct (i.e. AR1000 carrying pCambia 1301 lacking the cassette for hDAT expression). DAT+ are control 1°HRs expressing the hDAT (i.e. transformed with *A. rhizogenes* carrying AR1000 pCambia1301 carrying the cassette for constitutive expression of hDAT), but not mutated, and not selected—these controls do not differ from wild-type hairy roots (DAT-) in DAT inhibitory activity. The ATM population is of transgenic hDAT hairy roots that have been mutated, but not selected, and the RHR population (MPP+-resistant hairy roots) are transgenic hDAT mutants that have been selected on MPP+ (4 months) before removal to normal medium (2 months) (note: ATM and RHR populations are 2°HRs with gain-of-function mutations that functionally express the hDAT, but only RHRs were subject to selection on plant growth medium containing MPP+). As predicted, the ATM population shows a greater range of inhibition of DAT uptake than the DAT+ controls (3.96% of the ATM extracts produce DAT inhibition above the control range however the mean is not significantly different from controls). This trend is much greater in the RHR population in which 51.48% of the population contained extracts whose DAT inhibitory activity is above the control range, and the mean is significantly greater than any other population (One-way ANOVA, Tukey's Post-hoc test, p<0.0001 versus all other groups). The mean of this population is high partly because 11 individual cultures are well off-scale in FIG. 1—see FIG. 3 for more complete data). The effect of selection is immediately apparent from the difference in frequency of individuals above the DAT+ control range in the ATM population as compared to the RHR population, thus 26.73% of the RHR extracts produce DAT inhibitory activity above the ATM range. Remarkably, the inhibitory effect of 7 RHR extracts could not be expressed in lobinaline equivalents, since the extracts produced complete inhibition of dopamine uptake, whereas lobinaline produces a maximum inhibition of 85.25%. Therefore the selection procedure has greatly enriched a mutant sub-population in individuals over-producing metabolites which interact with the human target protein to cause functional inhibition. Importantly, inhibition observed in the RHR population was due to plant metabolites present in extracts prepared from individual cultures. Therefore, the inhibitory activity observed in this assay must represent "true positives", as opposed to survival due to knock-out or silencing of the hDAT gene.

Anti-Oxidant Activity Contained in Culture Extracts:

the ATM mutant group shows a few individuals with anti-oxidant activity above the control range, and the mean is higher, but not significantly so. The MPP+-resistant hairy root RHR extracts also show individuals above the control range and the mean is significantly higher than the control mean, but the difference is only two fold. These modest increases could be a consequence of increased levels of lobinaline in the resistant population. Thus, increases in anti-oxidant metabolites may play some role in the MPP+-resistance of individual mutants, but this is probably not great. A large proportion of the MPP+-resistant transgenic mutants appear to be over-producing metabolites which interact with the specific human target protein, in this case the hDAT.

Chemical Analysis of Culture Extracts by GC/MS

Figure 2:
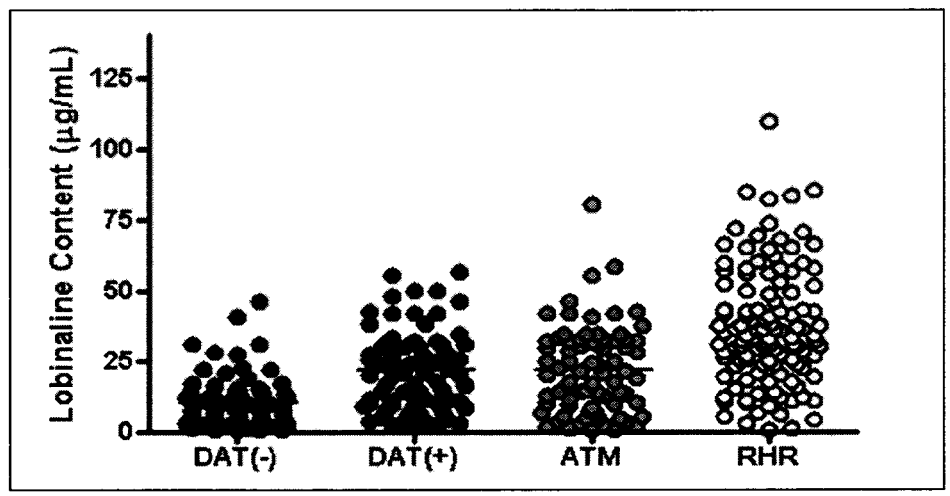
FIG. 2. Scattergram of lobinaline concentration (measured by GC/MS) in extracts of *L. cardinalis* hairy roots from different populations. The same convention is followed as for FIG. 1 in which DAT(−) and DAT(+) are controls, either not-expressing or expressing the hDAT respectively, ATM are transgenic hDAT hairy roots which have been mutated but not selected and RHR are transgenic hDAT mutant hairy roots which have been generated under selection in 100 uM MPP+. The mean of this population is significantly greater than that of any of the other populations.

Enhanced DAT inhibitory activity in MPP+-resistant transgenic mutants may be a consequence of over-production of lobinaline, or structurally related alkaloids. A GC-MS system that detects these alkaloids (as well as lobeline and MPP+) [21], was applied to representative culture extracts from each population. Lobinaline, purified as described above, was used as a standard, and produced a single peak at 18.26 minutes with an MS consistent with the previously reported GC-MS data [21]. In all control hairy roots (either DAT+ or DAT−) lobinaline was the major peak present with relatively little variation. Only a relatively small number (4.05%) of the ATM mutants overproduce lobinaline in excess of the DAT+ control range (see, FIG. 2). This is in contrast to the RHR mutants, where a large proportion (26.09%) were found to be overproducing lobinaline in excess of the control range (see, FIG. 2). Again, the selection process greatly enriched the population with a bioactive metabolite active at a specific target protein, in this case, the bioactive metabolites present in the wild-type plant. It is likely therefore, that lobinaline overproduction explains both the MPP+-resistance, and the DAT inhibitory, phenotypes of this sub-population of resistant mutants. However, several MPP+-resistant mutants which were not overproducing lobinaline showed an increased production of another peak (RT 14.4 minutes) with a different MS from that of lobinaline (the MS shows some similarity to that of dihydrolobinaline [21], but is not identical). This peak, and its MS, were not detectable in extracts of the wild-type plant, but were sometimes observed in other hairy root extracts. This peak was always associated with increased DAT inhibition, and so is likely to be relevant to the pharmacological phenotype of these cultures. In some of the cultures in which RT14.4 was increased, there were also marked increases in other minor peaks, including peaks at RT10.00 and 11.97 minutes which were not seen in controls. The MS of RT11.97 contains peaks which suggest an N-methylated piperidine alkaloid with a lower MW than lobinaline. Neither lobeline (which is a much simpler alkaloid than lobinaline) nor MPP+ were detectable in extracts from any of the cultures in any population analyzed thus far.

Figure 3:
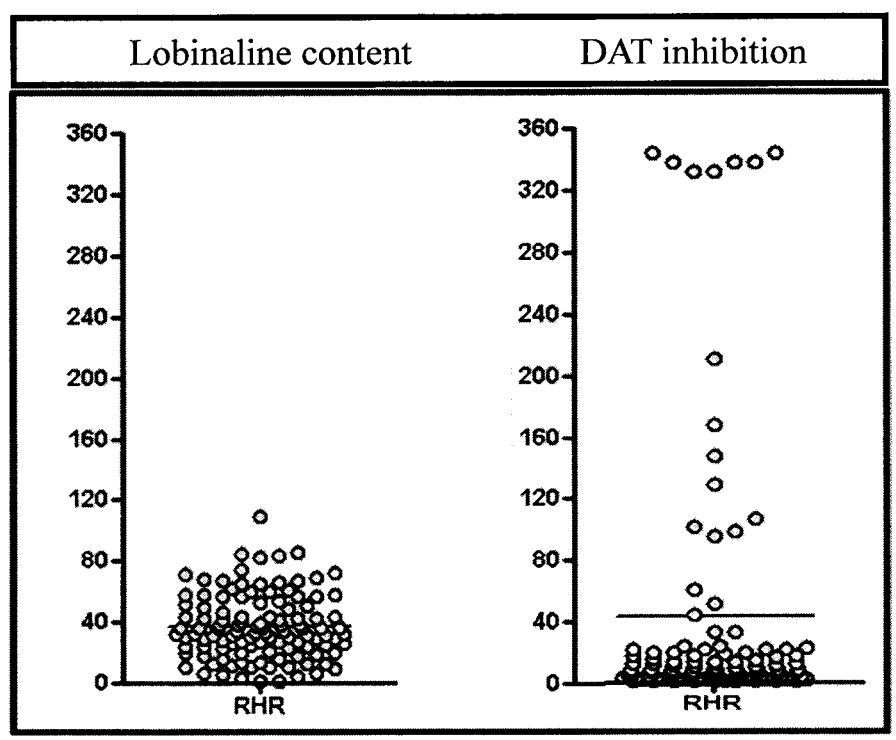
FIG. 3. Comparison of the scattergrams for lobinaline concentration (on left) and inhibition of [3H]dopamine uptake (on right) of extracts obtained from the transgenic (hDAT) mutant population which was generated under MPP+ selection. The expression of the latter as "lobinaline equivalents" enables a direct comparison. Although the means of the populations are very similar the distribution within the population clearly differs and there are many individuals in which inhibition of [3H]dopamine uptake is greater than can be explained by lobinaline content alone.

Comparisons Between DAT Inhibition and Lobinaline Content of Extracts from MPP+-Resistant Mutants The expression of DAT inhibition of culture extracts as "lobinaline equivalents" allows a direct comparison between the lobinaline content and DAT inhibition of the MPP+-resistant population. The data are shown in FIG. 3 with DAT inhibition far right. Although the means and SEM of lobinaline content and DAT inhibition are comparable (37.12+1.97 µg/mL vs 43.52+8.86 µg/mL, respectively) there are clear differences between the distribution of the data within this population. For example there are 11 extracts which show DAT inhibition above the range of lobinaline concentrations. It is highly unlikely that DAT inhibition in these cultures can be due solely to the presence of lobinaline. Indeed, when lobinaline concentration is plotted against DAT inhibition in lobinaline equivalents for all the individuals in this population there is a very low (non-significant) correlation between these measures. This indicates that there are likely to be other metabolites with inhibitory activity at the DAT that are being overproduced in these MPP+-resistant mutants. There are also likely to be mechanisms for resistance other than increased DAT inhibition represented in this population (see below).

Different Sub-Populations in the MPP+-Resistant Mutant Population

Based on the complete analysis of 107 individual mutant cultures in the MPP+-resistant population (for unknown reasons, 13 RHRs died when removed from selection) there are several sub-populations that can be identified. First, there are at least 16 individual mutants which are lobinaline over-producers compared to control groups. These mutant cultures are potentially valuable as sources of lobinaline, either in culture bioreactor systems, or as regenerated mutant plant lines. Regeneration of the 5 highest lobinaline over-producers is now in progress. Second, there are 25 individuals which have increased DAT inhibitory activity which cannot be due to their lobinaline content alone. Of these, 11 have high DAT inhibitory activity which is off-scale relative to all other cultures (11 cannot be expressed in lobinaline equivalents; expressed as maximum that could be extrapolated from lobinaline concentration response curve for DAT inhibition) (see FIG. 3). Extracts of another 2 mutants caused DAT inhibition 5× the SD above the control mean, but lobinaline content was less than that the control mean. It is highly likely that these contain previously uninvestigated metabolites with DAT inhibitory activity. These mutants therefore facilitate the discovery of natural products with a specific pharmacological activity. There are an additional 11 mutants which have DAT inhibitory activity more than 5× above SD of mean DAT inhibitory activity of non-selected mutants, but have normal levels of lobinaline. These mutants are likely to contain previously univestigated active metabolites in addition to lobinaline. Of particular interest regarding the synthesis of putatively novel DAT inhibitors, 3 mutants were found to synthesize a lobinaline congener (MS data display a pattern that is distinct from that of lobinaline, but does have peaks that are common to both alkaloids) that elutes ~6 seconds after lobinaline on GC traces. All 3 of these mutants extracts cause DAT inhibition that is 5× the SD above the control mean and is not explained by lobinaline. Thirdly, there are 5 individuals which are MPP+-resistant, but which show no increase in DAT inhibitory activity, or lobinaline content, in extracts derived from these cultures. This does not necessarily mean that DAT inhibition is not the mechanism for MPP+-resistance—some of these mutants are overproducing squalene and/or unsaturated lipids (GC/MS identification) that may both indirectly inhibit the DAT and reduce the cytotoxic mechanism of MPP+[29-31]. Of the 36 mutants which overproduce squalene, 25 (69.44%) produce DAT inhibition that is greater than 5×SD above the control mean. The 11 which overproduce squalene likely survive due to its ability to scavenge free radicals, or stabilize membranes [29]. These mechanisms are directly relevant to novel therapeutic approaches to dopaminergic neurodegeneration and show that the approach can identify completely unexpected protective cellular responses that are relevant to human disease. There are undoubtedly other unknown mechanisms for MPP+-resistance in this sub-population, some of which may be relevant to neurodegeneration, for example the activation of cytoprotective genes which have homology between plant and human genes [32, 33]. This is likely the case for 2 mutants that display DAT inhibition and lobinaline content below control means, and GC traces from each do not display any metabolites that are overproduced, or undetectable in controls.

Conclusions from the Selected Mutant Population

As described herein, the aim of these experiments was to show that the expression of a human target protein in plant cells could be used to direct the metabolism of mutant cells toward a specific pharmacological phenotype, in this case over-production of metabolites which inhibit the human dopamine transporter. As described in the results above, this aim was achieved. In addition, it was predicted that some of the mutants selected for this activity would be over-producing the major active metabolite in the wild-type plant, i.e. lobinaline, whereas others would be over-producing other unknown and uninvestigated active metabolites. As described in the results, this prediction has also been validated. Finally, there were several unexpected findings in the mutant population that may prove to be valuable to the understanding of eukaryotic protection against neurotoxins, and to the treatment of human neuro-degeneration. The research described in this example supports the value of heterologous target-directed biosynthesis coupled with selection of mutants as a powerful platform for plant drug discovery and plant drug production.

Example 2

Target-Directed Biosynthesis for Therapeutic Optimization of Medicinal Plant Species The methods described herein are designed to generate compounds which interact with specific target proteins (e.g., human target proteins), for use in conventional drug discovery, but uses plant biosynthesis rather than chemical synthesis to produce active molecules. The resulting "genomically optimized" mutant plant cells represent unique genetically-modified organisms. These plant cells are a source of individual active metabolites or of novel medicinal plant extracts.

The experiments described herein aim to establish the value of a modification of this technology, using phytoestrogens generated by licorice (*Glycyrrhiza glabra*) as the example. Licorice root extract is used worldwide as hormone replacement therapy post-menopause, because it contains phytoestrogens which activate human estrogen receptors (ERs). However, activity at the ERalpha subtype post-menopause is a potential cause of breast cancer, whereas activity at ERbeta is protective (Howell et al., Best practice & research Clinical endocrinology & metabolism. 2004; 18(1):47-66; Jiang et al., FASEB journal: official publication of the Federation of American Societies for Experimental Biology. 2013; 27(11):4406-18. doi: 10.1096/fj.13-234617). Licorice root extracts with increased levels of ERbeta-selective metabolites should therefore have a therapeutic and commercial advantage. To this end, plant cells have been transformed with human ERbeta linked to expression of a bacterial kanamycin resistance gene (construct 1), or ERalpha linked to expression of a yeast gene, dao1, which causes specific D-amino acids to become cytotoxic (construct 2). Construct 1 should increase the survival in kanamycin of cultures synthesizing ERbeta agonists, whereas construct 2 should reduce the survival in D-amino acids of cultures synthesizing ERalpha agonists. Thus, these constructs are co-expressed in licorice hairy root cultures, and a gain-of-function mutant population are generated, which are selected for survival in kanamycin and D-amino acids. The novel co-expression of these two constructs create intense survival pressure in favor of mutants that synthesize metabolites with relatively low ERalpha, and high ERbeta, agonist activity. Extracts of surviving cultures are analyzed for ER subtype agonist activity (reporter gene expression), and chemical analysis of phytoestrogens (HPLC). Based on previous studies, several of the surviving "genomically optimized" mutant cultures should contain active compounds that are not detectable in the wild-type plant.

As described herein, certain embodiments of the invention are used for discovering and producing drugs in plant cells. One major commercial advantage of this technology is that it generates molecules and plant extracts which can form the basis for treatments in either Western or traditional Asian medicine. The experiments described herein use the optimization of licorice root extract, used worldwide for suppression of menopausal symptoms, as an example of these methods.

Genomic Optimization of Soybean Toward an Optimal ER Pharmacological Phenotype:

Soy extracts are commonly used as estrogen supplements, and contain a mixture of phytoestrogens including the isoflavones like genistin (which are non-ER subtype selective), and flavonols, like kaempferol, which are somewhat ERbeta selective. The balance in ER activity is changed either by increasing flavonol synthesis (genetic engineering) or by selecting mutants for increased ERbeta activity (method described herein). For the former, transgenic soy hairy roots expressing a foreign flavonol synthase gene were generated, whereas for the latter, soy hairy root cultures were transformed with a construct in which the ligand binding site of human ERβ was linked to expression of a bacterial gene conferring kanamycin resistance (kr).

The transgenic hairy roots expressing construct 1 were killed by kanamycin unless ERβ ligands (agonists) were added to the medium. Random "gain of function" mutations were then produced in the ERbeta/kr hairy roots and the mutants selected for survival in kanamycin. Resistant mutants from this population were then compared with the transgenic flavonol synthase cultures, and with wild-type hairy roots. Flavonoid analysis by HPLC, showed that flavonol synthase transgenic cultures contain increased levels of flavonols, such as kaempferol, at the expense of isoflavones such as genistin. In contrast, the kanamycin-resistant transgenic mutants showed increases in both flavonols and isoflavones. Neither approach resulted in a marked difference in the relative ERalpha/ERbeta selectivity of crude extracts. In hindsight this is not surprising because none of the phytoestrogens naturally present in soy are very subtype selective. Accordingly, in addition to a selection pressure toward ERbeta activity, is another mechanism is needed which will drive secondary metabolism away from ERalpha activity. Therefore, a construct in which ERalpha activation would lead to cell death was developed. It is difficult to test such a construct in soy cultures because the major phytoestrogen is active at ERalpha, however, this is tested in licorice hairy roots, where the major phytoestrogen is relatively ERbeta selective.

Development of the ERalpha/Dao1 Construct:

The ERalpha/dao1 construct was generated by cloning the ligand-binding domain of the human ERalpha gene in a plasmid vector downstream to the GAL4 DNA-binding domain and the trans-activation protein VP16. All three DNA fragments were cloned as a translational fusion to form a single protein containing all three active domains. The effector cassette containing yeast dao1 gene was assembled in a separate vector. The yeast dao1 gene sequence was obtained from NCBI database (GenBank: U60066.1) and primers were designed to isolate the full-length cDNA of dao1 gene from yeast *Rhodosporidium toruloides* Banno (ATCC 26217).

Construct 2 has been generated, will be characterized prior to its transformation into plant cells. When this construct is expressed in plant cells it should confer cytotoxicity by exposure to D-valine and D-isoleucine in cells which are overproducing agonists at ERalpha. This is because these D-amino acids are metabolized into toxic products by the dao1 gene product. Mutant plant cells with low levels of ERalpha agonists should be unaffected by these amino acids.

LITERATURE CITED

1. Watanabe, Y., T. Himeda, and T. Araki, *Mechanisms of MPTP toxicity and their implications for therapy of Parkinson's disease*. Med Sci Monit, 2005. 11(1): p. RA17-23.
2. Nutt, J. G., J. H. Carter, and G. J. Sexton, *The dopamine transporter: importance in Parkinson's disease*. Ann Neurol, 2004. 55(6): p. 766-73.
3. Rothman, R. B., et al., *Dopamine transport inhibitors based on GBR12909 and benztropine as potential medications to treat cocaine addiction*. Biochem Pharmacol, 2008. 75(1): p. 2-16.
4. Iversen, L., *Neurotransmitter transporters: fruitful targets for CNS drug discovery*. Mol Psychiatry, 2000. 5(4): p. 357-62.
5. Kristensen, A. S., et al., *SLC6 neurotransmitter transporters: structure, function, and regulation*. Pharmacol Rev, 2011. 63(3): p. 585-640.
6. Gether, U., et al., *Neurotransmitter transporters: molecular function of important drug targets*. Trends Pharmacol Sci, 2006. 27(7): p. 375-83.
7. Zhang, F. Q., Z. P. Luo, and Z. H. Gong, *Desipramine and fluoxetine antagonized 5,7-dihydroxytryptamine-induced lesion on rat hippocampal and cortical neurons*. Zhongguo Yao Li Xue Bao, 1999. 20(10): p. 889-92.
8. Cederbaum, A. I., *Alcohol metabolism*. Clin Liver Dis, 2012. 16(4): p. 667-85.
9. Saji, S., M. Hirose, and M. Toi, *Clinical significance of estrogen receptor beta in breast cancer*. Cancer Chemother Pharmacol, 2005. 56 Suppl 1: p. 21-6.
10. Pinkerton, J. V., D. W. Stovall, and R. S. Kightlinger, *Advances in the treatment of menopausal symptoms*. Womens Health (Lond Engl), 2009. 5(4): p. 361-384; quiz 383-4.
11. Perry, C. J. and A. B. Barron, *Neural mechanisms of reward in insects*. Annu Rev Entomol, 2013. 58: p. 543-62.
12. Kawamata, J., S. Suzuki, and S. Shimohama, *alpha7 nicotinic acetylcholine receptor mediated neuroprotection in Parkinson's disease*. Curr Drug targets, 2012. 13(5): p. 623-30.
13. Xi, Z. X., K. Spiller, and E. L. Gardner, *Mechanism-based medication development for the treatment of nicotine dependence*. Acta Pharmacol Sin, 2009. 30(6): p. 723-39.
14. Rahman, S. and M. A. Prendergast, *Cholinergic receptor system as a target for treating alcohol abuse and dependence*. Recent Pat CNS Drug Discov, 2012. 7(2): p. 145-50.
15. Zhu, J. and M. E. Reith, *Role of the dopamine transporter in the action of psychostimulants, nicotine, and other drugs of abuse*. CNS Neurol Disord Drug targets, 2008. 7(5): p. 393-409.
16. Runyon, S. P. and F. I. Carroll, *Dopamine transporter ligands: recent developments and therapeutic potential*. Curr Top Med Chem, 2006. 6(17): p. 1825-43.
17. Littleton, J., T. Rogers, and D. Falcone, *Novel approaches to plant drug discovery based on high throughput pharmacological screening and genetic manipulation*. Life Sci, 2005. 78(5): p. 467-75.
18. Littleton, J., *The future of plant drug discovery*. Expert Opin Drug Discov, 2007. 2(5): p. 673-83.
19. Davies, A. R., et al., *Characterisation of the binding of [3H]methyllycaconitine: a new radioligand for labelling alpha 7-type neuronal nicotinic acetylcholine receptors*. Neuropharmacology, 1999. 38(5): p. 679-90.
20. Manske, R. H. F., *LOBINALINE, AN ALKALOID FROM LOBELIA CARDINALIS L.* Canadian Journal of Research, 1938. 16b(12): p. 445-448.
21. Clugston, D. M., D. B. MacLean, and R. H. F. Manske, *The examination of lobinaline and some degradation products by mass spectrometry*. Canadian Journal of Chemistry, 1967. 45(1): p. 39-47.
22. Felpin, F.-X. and J. Lebreton, *History, chemistry and biology of alkaloids from Lobelia inflata*. Tetrahedron, 2004. 60(45): p. 10127-10153.
23. Cassarino, D. S., et al., *The parkinsonian neurotoxin MPP+ opens the mitochondrial permeability transition pore and releases cytochrome c in isolated mitochondria via an oxidative mechanism*. Biochim Biophys Acta, 1999. 1453(1): p. 49-62.
24. Tsugawa, H., T. Kagami, and M. Suzuki, *High-frequency transformation of Lobelia erinus L. by Agrobacterium-mediated gene transfer*. Plant Cell Rep, 2004. 22(10): p. 759-64.
25. Jefferson, R. A., T. A. Kavanagh, and M. W. Bevan, *GUS fusions: beta-glucuronidase as a sensitive and versatile gene fusion marker in higher plants*. EMBO J, 1987. 6(13): p. 3901-7.
26. Storch, A., et al., *6-Hydroxydopamine toxicity towards human SH-SY5Y dopaminergic neuroblastoma cells: independent of mitochondrial energy metabolism*. Journal of Neural Transmission, 2000. 107(3): p. 281-293.
27. Andoh, T., et al., *Role of the redox protein thioredoxin in cytoprotective mechanism evoked by (−)-deprenyl*. Mol Pharmacol, 2005. 68(5): p. 1408-14.
28. Hayashi, H., et al., *Activation of a plant gene by T-DNA tagging: auxin-independent growth in vitro*. Science, 1992. 258(5086): p. 1350-3.
29. Kabuto, H., et al., *Effects of squalene/squalane on dopamine levels, antioxidant enzyme activity, and fatty acid composition in the striatum of Parkinson's disease mouse model*. J Oleo Sci, 2013. 62(1): p. 21-8.
30. Bousquet, M., et al., *Transgenic conversion of omega-6 into omega-3 fatty acids in a mouse model of Parkinson's disease*. J Lipid Res, 2011. 52(2): p. 263-71.
31. Chen, N., et al., *Inhibition by arachidonic acid and other fatty acids of dopamine uptake at the human dopamine transporter*. Eur J Pharmacol, 2003. 478(2-3): p. 89-95.
32. Xu, X. M. and S. G. Moller, *The value of Arabidopsis research in understanding human disease states*. Curr Opin Biotechnol, 2011. 22(2): p. 300-7.
33. Jones, A. M., et al., *The impact of Arabidopsis on human health: diversifying our portfolio*. Cell, 2008. 133(6): p. 939-43.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of selecting a mutant plant cell that overproduces a metabolite that activates an estrogen receptor (ER) beta but does not activate an ER alpha; the method comprising transforming cells from a plant with:
   a) a first vector comprising a polynucleotide encoding a heterotrimeric fusion protein comprising an ER beta ligand binding domain, a transcription factor DNA binding domain, and a transactivating transcriptional activator domain;
   b) a selection marker operably linked to a promoter that contains responsive elements causing activation by the heterotrimeric protein encoded by the first vector in the presence of the metabolite;
   c) a second vector comprising a polynucleotide encoding a heterotrimeric fusion protein comprising an ER alpha ligand binding domain, a transcription factor DNA binding domain, and a transactivating transcriptional activator domain; and
   d) a nucleic acid encoding the yeast dao1 "cell death" protein, wherein the nucleic acid is operably linked to a promoter that contains responsive elements causing activation by the heterotrimeric protein encoded by the second vector in the presence of ER alpha activators; to arrive at transformed plant cells comprising the first vector, the selection marker, the second vector, and the nucleic acid encoding the yeast dao1 protein;

the method further comprising mutagenizing the resulting transformed cells and exposing the resulting mutant transgenic cells to a first compound that corresponds to the selection marker, and exposing the cells to D-valine or D-isoleucine; wherein mutant cells that overproduce a metabolite that activates ER beta survive exposure to the first compound, and wherein mutant cells that overproduce a metabolite that activates ER alpha do not survive exposure to D-valine or D-isoleucine; whereby the resulting mutant cell overproduces the metabolite relative to a non-mutant cell of the same species.

2. The method of claim 1, wherein the plant cell is a *Lobelia cardinalis, Hypericum punctatum, Nicotiana tabacum, Glycine max* or *Glycyrrhiza glabra* plant cell.

3. The method of claim 1, wherein cells from the plant are transformed by infecting the cells with Agrobacteria comprising the first and/or second vector.

4. The method of claim 1, wherein the transformed cells are mutagenized by activation tagging mutagenesis (ATM).

5. The method of claim 1, further comprising identifying the one or more activators or inhibitors that are overproduced in the mutagenized transgenic cells.

6. A transgenic plant cell, cell line, or plant comprising the first vector, the selection marker, the second vector, and the nucleic acid from parts a-d of claim 1.

* * * * *